United States Patent
Chen et al.

(10) Patent No.: US 10,106,557 B2
(45) Date of Patent: Oct. 23, 2018

(54) PREPARATION METHOD FOR BENZOXAZOLEOXAZINE KETONE COMPOUND AND INTERMEDIATE AND CRYSTAL FORM THEREOF

(71) Applicant: NORTH CHINA PHARMACEUTICAL NEW DRUG R & D CO., LTD., Shijiazhuang, Hebei (CN)

(72) Inventors: Shuhui Chen, Shanghai (CN); Zhaozhong Ding, Shanghai (CN); Gangli Gong, Shanghai (CN); Xiaobing Yan, Shanghai (CN); Wei Huang, Shanghai (CN); Feng Guo, Shanghai (CN); Baoling Duan, Shijiazhuang (CN); Renlong Gao, Shijiazhuang (CN); Pingfan Zhou, Shijiazhuang (CN); Xinhua Lu, Shijiazhuang (CN); Guimin Dong, Shijiazhuang (CN)

(73) Assignee: NORTH CHINA PHARMACEUTICAL NEW DRUG R&D CO., LTD., Shijiazhuang (CN)

(*) Notice: Subject to any disclaimer, the term of this patent is extended or adjusted under 35 U.S.C. 154(b) by 0 days.

(21) Appl. No.: 15/514,326

(22) PCT Filed: Sep. 23, 2015

(86) PCT No.: PCT/CN2015/090334
§ 371 (c)(1),
(2) Date: Mar. 24, 2017

(87) PCT Pub. No.: WO2016/045586
PCT Pub. Date: Mar. 31, 2016

(65) Prior Publication Data
US 2017/0275299 A1 Sep. 28, 2017

(30) Foreign Application Priority Data
Sep. 26, 2014 (CN) .......................... 2014 1 0503772

(51) Int. Cl.
C07D 498/14 (2006.01)
C07D 265/32 (2006.01)

(52) U.S. Cl.
CPC ......... *C07D 498/14* (2013.01); *C07D 265/32* (2013.01); *C07B 2200/13* (2013.01)

(58) Field of Classification Search
CPC .............................................. C07D 498/14
USPC .................................................. 544/101
See application file for complete search history.

(56) References Cited

U.S. PATENT DOCUMENTS 8,507,481 B2    8/2013  Yang et al.

2007/0149522 A1  6/2007 Thomas
2013/0123249 A1  5/2013 Yang et al.

FOREIGN PATENT DOCUMENTS

| CN | 103936763 A | 7/2014 |
| CN | 105503903 A | 4/2016 |
| EP | 2947085 A1 | 11/2015 |
| EP | 3199536 A1 | 8/2017 |
| WO | WO-2001002020 A2 | 1/2001 |
| WO | WO-2011147259 A1 | 12/2011 |

OTHER PUBLICATIONS

Xin et al. Journal of Medicinal Chemistry (2011), 54(21), 7493-7502.*
International Search Report for PCT/CN2015/090334, ISA/CN, Beijing, dated Dec. 25, 2015.
Qisheng Xin et al., "Design, Synthesis, and Structure-Activity Relationship Studies of Highly Potent Novel Benzoxazinyl-Oxazolidinone Antibacterial Agents", Journal of Medicinal Chemistry, vol. 54, pp. 7493-7502, 2011.
Yingjie Cui et al., "Stereocontrolled Synthesis of Tricyclic Fused Oxazolidinone as Antibacterial Agent", J. Heterocylic Chem, vol. 43, p. 1071, 2006.
Loretta L. et al., "Multikilogram Synthesis of 4-D-Erythronolactone via Batch and Continuous Processing", Organic Process Research & Development, vol. 16, pp. 1003-1012, 2012.
Theodora W. Greene et al., "Protective Groups in Organic Synthesis", 1991.
Gerrit Limberg et al., "Preparation of the Four Stereoisomeric 4-Amino-3-hydroxypyrrolidines from Bromodeoxytetronic Acids. Discovery of a New á-Mannosidase Inhibitor", No. 1, pp. 178-183, 1999.
Dec. 25, 2015 Written Opinion of the International Searching Authority issued in International Patent Application No. PCT/CN2015/090334.
Tao Xue et al., "Design, Synthesis, and Structure-Activity and Structure-Pharmacokinetic Relationship Studies of Novel [6,6,5] Tricyclic Fused Oxazolidinones Leading to the Discovery of a Potent, Selective, and Orally Bioavailable FXa Inhibitor", Journal of Medicinal Chemistry, vol. 57, No. 18, Sep. 2, 2014.
Extended European Search Report dated Jun. 29, 2018.

* cited by examiner

*Primary Examiner* — Kahsay Habte
(74) *Attorney, Agent, or Firm* — Harness, Dickey & Pierce, P.L.C.

(57) ABSTRACT

A preparation method for a high-purity benzoxazoleoxazine ketone compound, a crystal form thereof, and an intermediate compound for preparing a compound of formula (I), and a preparation method therefor.

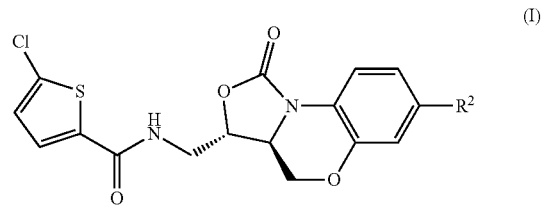

(I)

8 Claims, 2 Drawing Sheets

PREPARATION METHOD FOR BENZOXAZOLEOXAZINE KETONE COMPOUND AND INTERMEDIATE AND CRYSTAL FORM THEREOF

CROSS REFERENCE TO RELATED APPLICATIONS

This application is a U.S. National Phase Application under 35 U.S.C. 371 of International Application No. PCT/CN2015/090334 filed on Sep. 23, 2015 and published in Chinese as WO 2016/045586 A1 on Mar. 31, 2016. This application is based on and claims the benefit of priority from Chinese Patent Application No. 201410503772.7 filed Sep. 26, 2014. The entire disclosures of all of the above applications are incorporated herein by reference.

FIELD OF INVENTION

The present invention relates to a process for preparing high-purity benzoxazoleoxazine ketone compound, and a crystal form thereof, the present invention also relates to an intermediate compound used for preparing the compound having a structure of formula (I), and a preparation method therefor.

PRIOR ARTS

CN21310456006.5 discloses a series of novel Xa factor inhibitors for oral administration, which are used to prevent postoperative deep vein thrombosis (DVT) and pulmonary embolism (PE), prevent stroke upon atrial fibrillation, treat with acute coronary syndrome (ACS), having a structure of formula (B-1),

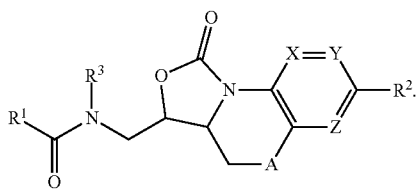

(B-1)

CONTENT OF THE PRESENT INVENTION

The present invention provides a process for preparing a compound having a structure of formula (I),

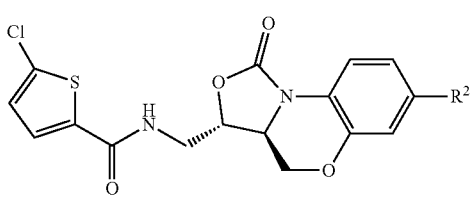

(I)

comprising

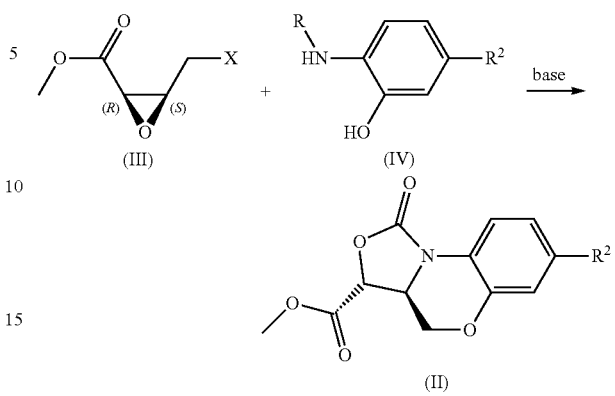

wherein R is an amino-protecting group;
X is F, Cl, Br or I;
$R^2$ is selected from an optionally substituted 5- or 6-membered cyclic amino or a heterocyclic amino, and "hetero" represents O, N, C(=O), C(=O)NH, the substituents are independently selected from a $C_{1-4}$ alkyl or a heteroalkyl.

In some embodiments of the present invention, R is selected from an alkoxycarbonyl which is an amino-protecting group.

In some embodiments of the present invention, R is selected from Cbz, Boc, Fmoc, Alloc, Teco, methoxycarbonyl or ethoxycarbonyl.

In some embodiments of the present invention, $R^2$ is selected from

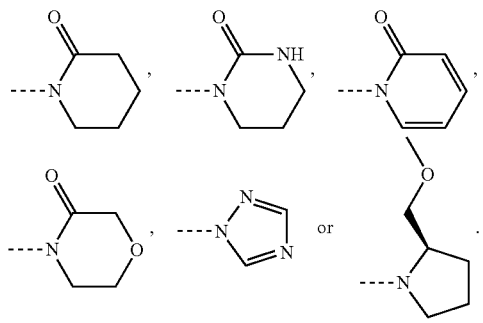

In some embodiments of the present invention, the base is selected from an alkali metal base, an alkaline earth metal base or an organometallic base.

In some embodiments of the present invention, the alkali metal base is selected from lithium hydroxide, sodium hydroxide, potassium hydroxide, cesium hydroxide, sodium carbonate, potassium carbonate, cesium carbonate, sodium bicarbonate and/or potassium bicarbonate.

In some embodiments of the present invention, the alkaline earth metal base is selected from sodium hydride, potassium hydride and/or calcium hydride.

In some embodiments of the present invention, the organometallic base is selected from sodium methoxide, lithium tert-butoxide, sodium tert-butoxide, potassium tert-butoxide, sodium ethoxide and/or aluminum isopropoxide.

In some embodiments of the present invention, a molar ratio of the compound (IV) to the base is 1:1 to 5, specifically 1:2 to 3.

In some embodiments of the present invention, a molar ratio of the compound (III) to the compound (IV) is 1:1 to 2.

In some embodiments of the present invention, temperature of the reaction is −10 to 50° C.

In some embodiments of the present invention, the temperature of the reaction is 0 to 30° C.

In some embodiments of the present invention, reaction time is 5 to 200 hours.

In some embodiments of the present invention, the reaction time is 10 to 100 hours.

In some embodiments of the present invention, the reaction time is 16 to 48 hours.

In some embodiments of the present invention, the reaction is carried out in a solvent, the solvent is selected from an amide solvent, an ether solvent or any mixture thereof.

In some embodiments of the present invention, an amount of the solvent is 10 to 50 times the weight of the compound (IV).

In some embodiments of the present invention, the amount of the solvent is 15 to 20 times the weight of the compound (IV).

In some embodiments of the present invention, the amide solvent is selected from DMF or DMAC.

In some embodiments of the present invention, the ether solvent is selected from tetrahydrofuran, methyl tetrahydrofuran, dioxane or methyl t-butyl ether.

In some embodiments of the present invention, the process for preparing the compound having a structure of formula (I) further comprises

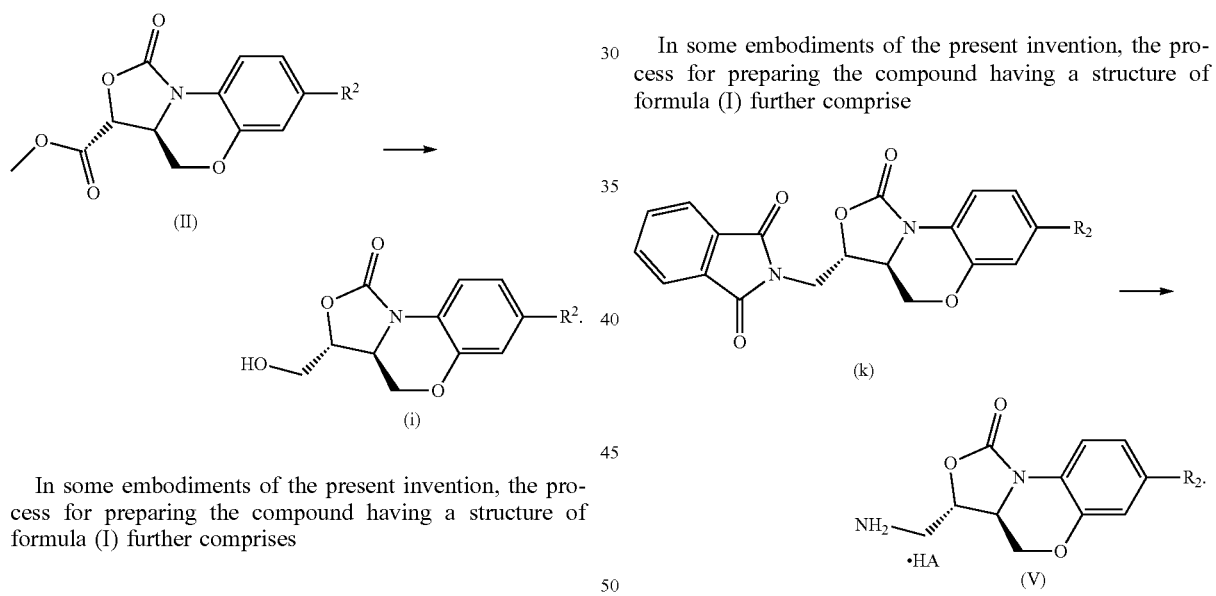

In some embodiments of the present invention, the process for preparing the compound having a structure of formula (I) further comprises

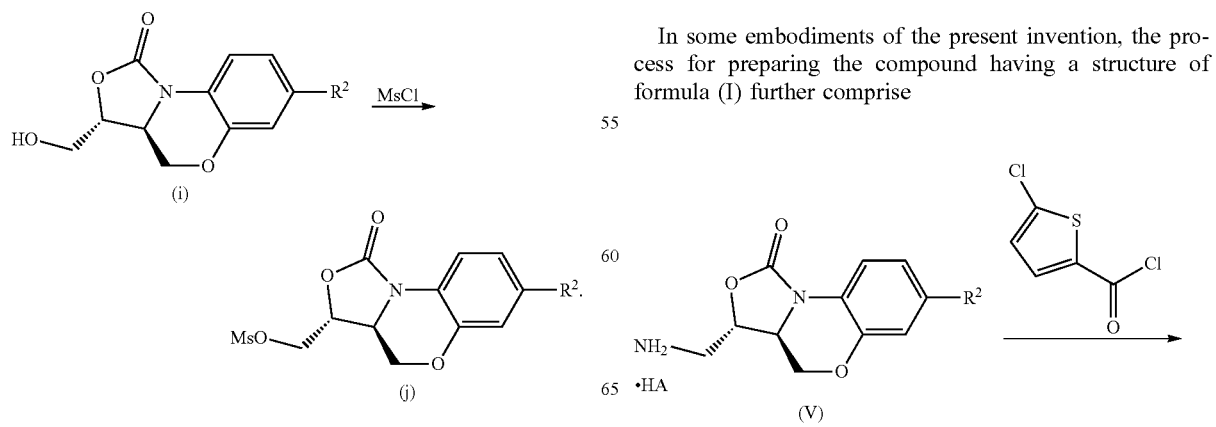

In some embodiments of the present invention, the process for preparing the compound having a structure of formula (I) further comprise

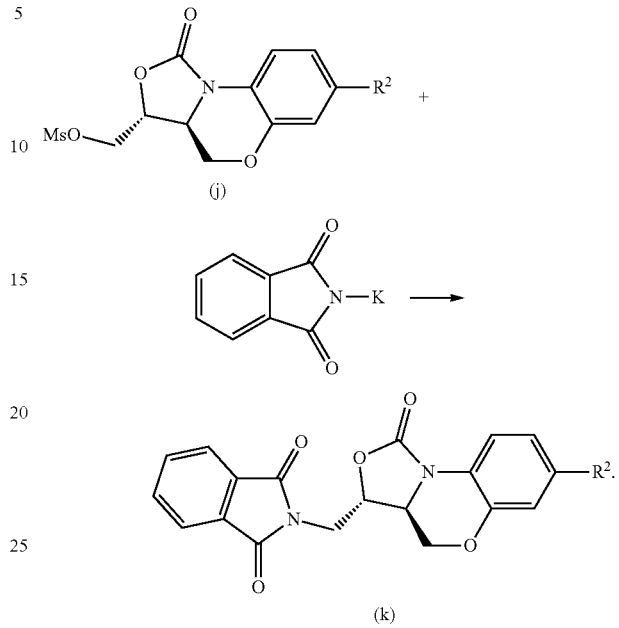

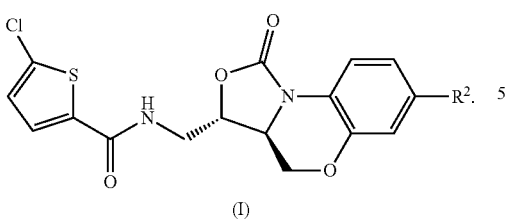

(I)

The process for preparing the compound having a structure of formula (I) further comprise

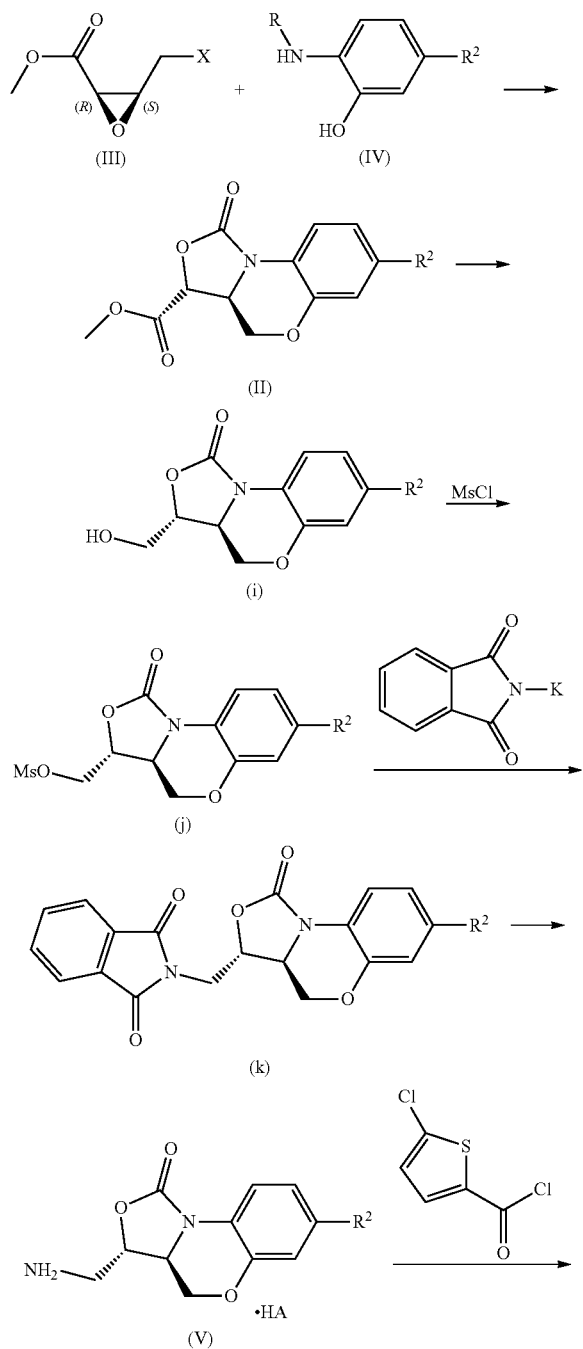

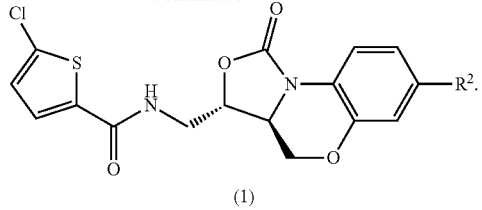

(1)

In some embodiments of the present invention, the HA is selected from an organic acid or an inorganic acid.

In some embodiments of the present invention, the HA is selected from hydrochloric acid, sulfuric acid, oxalic acid, citric acid, maleic acid or fumaric acid.

In some embodiments of the present invention, the compound (i) can be prepared by reacting the compound (II) with a reducing agent, wherein:

the reducing agent is preferably an alkali metal hydride;

the alkali metal hydride is preferably sodium borohydride, sodium triacetylborohydride, sodium cyanoborohydride, red aluminum and/or lithium aluminum tetrahydrate;

a molar ratio of the compound (II) to the reducing agent is preferably 1:1 to 5;

the reaction is carried out in a solvent, the solvent is preferably a single organic solvent or a mixed organic solvent;

the organic solvent is preferably methanol, ethanol, tetrahydrofuran and/or dichloromethane;

an amount of the solvent is 5 to 20 times the weight of the compound (II);

temperature of the reaction is −10 to 50° C.;

the temperature of the reaction is 0 to 30° C.;

reaction time is 2 to 30 hours;

the reaction time is 8 to 16 hours.

In some embodiments of the present invention, the compound (j) can be prepared by reacting the compound (i) with methanesulfonyl chloride in the presence of a base, wherein, the base is preferably an alkali metal base, an alkaline earth metal base, an organometallic base and/or an organic base;

the alkali metal base is preferably lithium hydroxide, sodium hydroxide, potassium hydroxide, cesium hydroxide, sodium carbonate, potassium carbonate, cesium carbonate, sodium bicarbonate and/or potassium bicarbonate;

the alkaline earth metal base is preferably sodium hydride, potassium hydride and/or calcium hydride;

the organometallic base is preferably sodium methoxide, lithium tert-butoxide, sodium tert-butoxide, potassium tert-butoxide, sodium ethoxide and/or aluminum isopropoxide;

the organic base is preferably diethylamine, triethylamine, DIEA, pyridine, DMAP and/or DBU;

a molar ratio of the compound (i) to the base is preferably 1:1 to 5;

a molar ratio of the compound (i) to the methanesulfonyl chloride is preferably 1:1 to 2;

the reaction is carried out in a solvent, the solvent is preferably an aprotic organic solvent;

the organic solvent is preferably benzene, toluene, dioxane, dichloromethane, tetrahydrofuran and/or methyl tetrahydrofuran;

an amount of the solvent is 5 to 20 times the weight of the compound (i);

temperature of the reaction is −20 to 50° C.;

the temperature of the reaction is preferably −5 to 15° C.;

reaction time is 2 to 30 hours;

the reaction time is 8 to 16 hours.

In some embodiments of the present invention, the compound (k) can be prepared by reacting the compound (j) with phthalimide potassium salt, or prepared by reacting the compound (j) with phthalimide potassium salt in the presence of a base, wherein, the base is preferably an alkali metal base, an alkaline earth metal base, an organometallic base and an organic base;

the alkali metal base is preferably lithium hydroxide, sodium hydroxide, potassium hydroxide, cesium hydroxide, sodium carbonate, potassium carbonate, cesium carbonate, sodium bicarbonate and/or potassium bicarbonate;

the alkaline earth metal base is sodium hydride, potassium hydride and/or calcium hydride;

the organometallic base is sodium methoxide, lithium tert-butoxide, sodium tert-butoxide, potassium tert-butoxide, sodium ethoxide and/or aluminum isopropoxide;

the molar ratio of the compound (j) to the base is preferably 1:1 to 5;

the reaction is carried out in a solvent, the solvent is preferably an aprotic organic solvent;

the organic solvent is benzene, toluene, dioxane, tetrahydrofuran, DMF, DMSO and/or NMP;

an amount of the solvent is 5 to 20 times the weight of the compound (i);

temperature of the reaction is 0 to 100° C.;

the temperature of the reaction is 20 to 80° C.;

reaction time is 2 to 30 hours;

the reaction time is 8 to 16 hours.

In some embodiments of the present invention, the compound (II) can be used for preparing the compound (V),

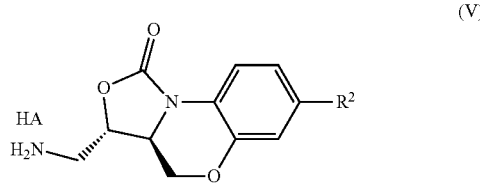

wherein, the compound (V) can be prepared by reacting the compound (j) with a base, followed by adding an acid to precipitate the salt, the base is preferably an alkali metal base or an organic base;

the alkali metal base is preferably lithium hydroxide, sodium hydroxide, potassium hydroxide, cesium hydroxide, sodium carbonate, potassium carbonate, cesium carbonate, sodium bicarbonate and/or potassium bicarbonate;

the organic base is preferably hydrazine hydrate, aqueous ammonia, an aqueous methylamine solution and/or a methylamine alcohol solution;

the acid is preferably an inorganic acid or an organic acid;

the inorganic acid is preferably hydrochloric acid or sulfuric acid;

the organic acid is preferably oxalic acid, citric acid, maleic acid and/or fumaric acid;

the molar ratio of the compound (j) to the base is preferably 1:2 to 10;

the molar ratio of the compound (j) to the acid is preferably 1:2 to 10;

the reaction is carried out in a solvent, the solvent is preferably water or a protic organic solvent;

the organic solvent is preferably methanol, ethanol and/or isopropanol;

an amount of the solvent is 5 to 20 times the weight of the compound (i);

temperature of the reaction is 0 to 100° C.;

the temperature of the reaction is 20 to 80° C.;

the reaction time is 2 to 30 hours.

In some embodiments of the present invention, the compound 1 can be prepared by reacting the compound (V) with 5-chlorothiophene-2-formyl chloride in the presence of a base, wherein, a molar ratio of the compound (V) to the base is preferably 1:1 to 3;

a molar ratio of the compound (V) to the 5-chlorothiophene-2-formyl chloride is preferably 1:1 to 2;

the reaction is carried out in a solvent, the solvent is preferably a mixed solvent of water and an organic solvent, the organic solvent is preferably an ether solvent or an aromatic solvent;

the ether solvent is preferably tetrahydrofuran or methyl tetrahydrofuran;

the aromatic solvent is preferably benzene, toluene, chlorobenzene or bromobenzene;

a volume ratio of water to the organic solvent is 1:1 to 2;

an amount of the solvent is 5 to 20 times the weight of the compound (V);

temperature of the reaction is 0 to 40° C., preferably 10 to 30° C.;

the reaction time is 5 to 30 hours.

5-Chlorothiophene-2-formyl chloride can be prepared by reference to the method disclosed in Example 1 of U.S. Patent Application US2007149522 filed by Bayer Healthcare AG, India. In particular, thionyl chloride was added into a solution of 5-chlorothiophene-2-carboxylic acid in toluene at 80° C. and the mixture was stirred for 2 to 3 hours, concentrated to give 5-chlorothiophene-2-formyl chloride.

The compound (III') can be prepared according to the following synthetic route:

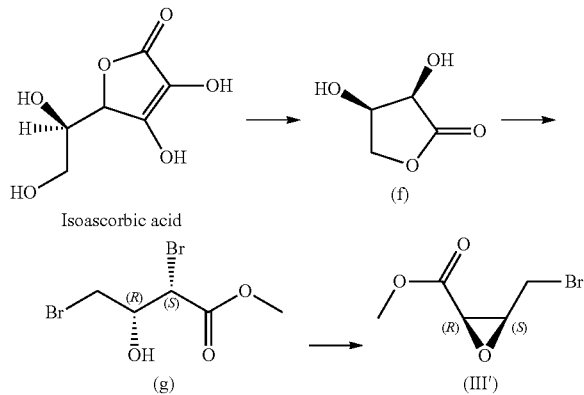

The compound (III') can also be prepared with the compound (g) according to the method disclosed in Synthesis, (1), 178-183; 1999.

The compound (g) can be prepared with the compound (f) or the compound (h) according to the method described in Indian Patent Document 2006MU00055, alternatively, the compound (g) may be prepared according to the following synthetic route.

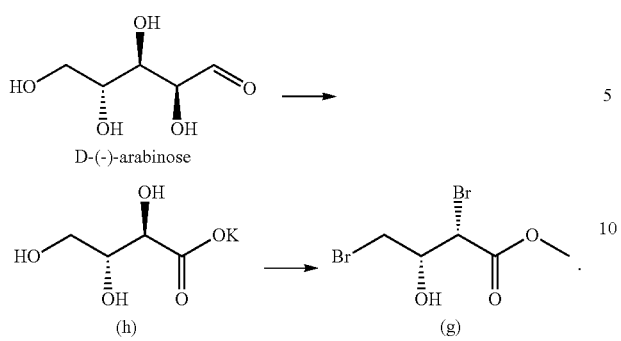

The compound (f) can be prepared with the natural product isoascorbic acid according to the method disclosed in Organic Process Research & Development, 16(5), 1003-1012; 2012.

The compound (h) can be prepared with the natural product D-arabinose according to the method disclosed in WO2001002020.

The present invention also provides an intermediate for preparing the compound (I), which has any one of the following structure:

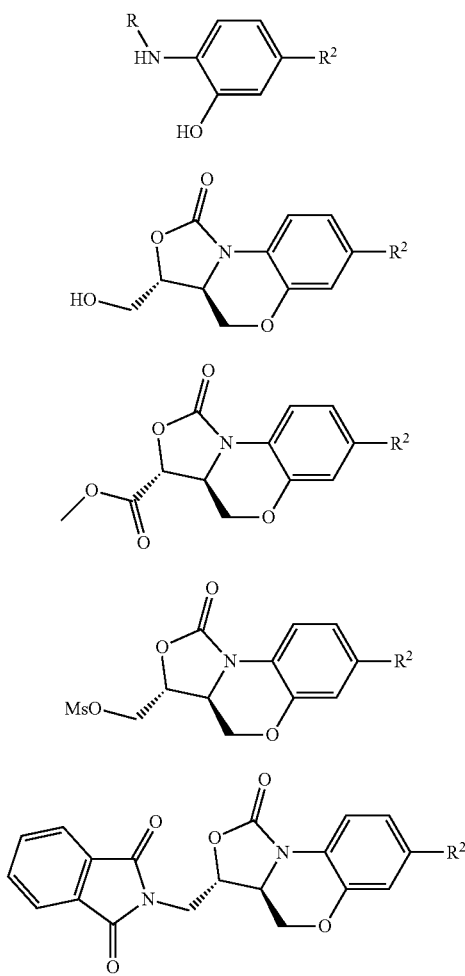

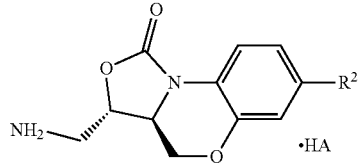

wherein,

R is an amino-protecting group;

R is selected from an alkoxycarbonyl, an amino-protecting group,

R is selected from Cbz, Boc, Fmoc, Alloc, Teco, methoxycarbonyl or ethoxycarbonyl, $R^2$ is selected from an optionally substituted 5- or 6-membered cyclic amino or heterocyclic amino, and "hetero" represents O, N, C(=O), or C(=O)NH, the substituent is independently selected from a $C_{1-4}$ alkyl or a heteroalkyl;

$R^2$ is selected from

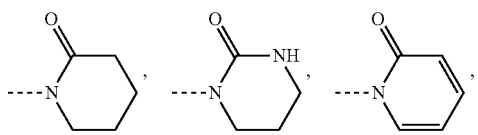

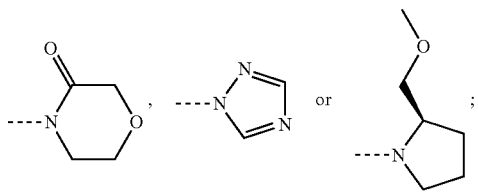

HA is selected from an organic acid or an inorganic acid;

HA is selected from hydrochloric acid, sulfuric acid, oxalic acid, citric acid, maleic acid or fumaric acid. The present invention also provides a process for preparing the intermediate (IV), comprising

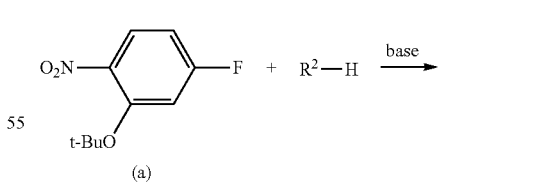

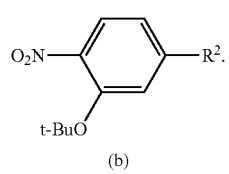

In some embodiments of the present invention, the process for preparing the intermediate (IV) further comprises

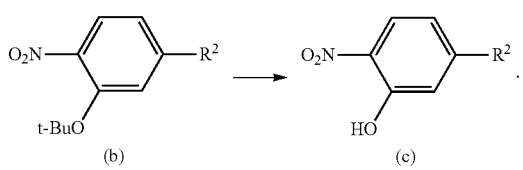

In some embodiments of the present invention, the process for preparing the intermediate (IV) further comprises

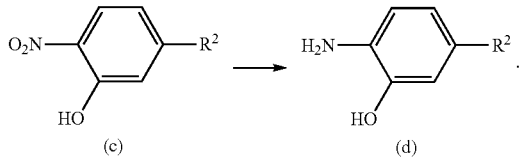

In some embodiments of the present invention, the process for preparing the intermediate (IV) further comprises

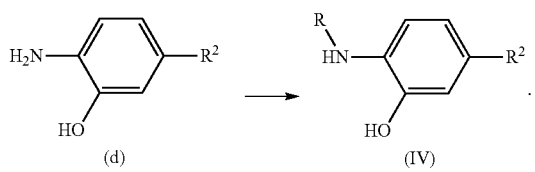

In some embodiments of the present invention, the process for preparing the intermediate (IV) further comprises

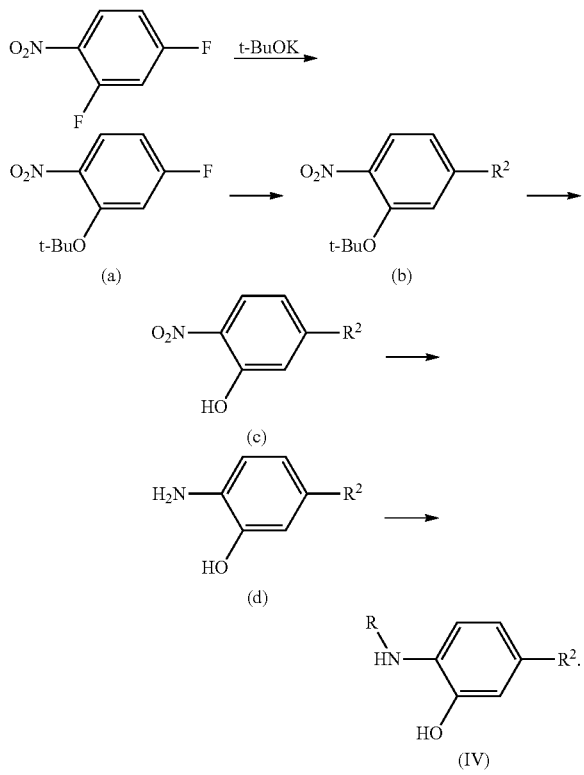

In some embodiments of the present invention, in the process for preparing the intermediate (IV), the compound (a) can be prepared by reacting 2,4-difluoronitrobenzene with potassium tert-butoxide, wherein, a molar ratio of 2,4-difluoronitrobenzene to potassium tert-butoxide is preferably 1:1 to 3;

the reaction is carried out in a solvent, the solvent is an organic solvent;

the organic solvent is preferably an ether solvent or an aromatic solvent;

the ether solvent is preferably tetrahydrofuran or methyl tetrahydrofuran;

the aromatic solvent is preferably benzene, toluene, chlorobenzene or bromobenzene;

an amount of the solvent is 5 to 20 times the weight of 2,4-difluoronitrobenzene;

temperature of the reaction is 0 to 40° C.;

the temperature of the reaction is 10 to 30° C.;

the reaction time is 1 to 30 hours;

the reaction time is 3 to 8 hours.

In some embodiments of the present invention, the compound (b) can be prepared by reacting the compound (a) with $R^2$—H in the presence of a base, wherein, the base is selected from an alkali metal base, an alkaline earth metal base or an organometallic base;

the alkali metal base is selected from lithium hydroxide, sodium hydroxide, potassium hydroxide, cesium hydroxide, sodium carbonate, potassium carbonate, cesium carbonate, sodium bicarbonate and/or potassium bicarbonate;

the alkaline earth metal base is selected from sodium hydride, potassium hydride and/or calcium hydride;

the organometallic base is selected from sodium methoxide, lithium tert-butoxide, sodium tert-butoxide, potassium tert-butoxide, sodium ethoxide and/or aluminum isopropoxide;

a molar ratio of the compound (a) to the base is 1:1 to 3;

a molar ratio of the compound (a) to $R^2$—H is 1:1 to 2;

the reaction is carried out in a solvent, the solvent is selected from a mixed solvent of a non-polar solvent and a polar solvent;

the non-polar solvent is selected from benzene, toluene, xylene chlorobenzene and/or bromobenzene;

the polar solvent is selected from DMF, DMSO or NMP;

a volume ratio of the non-polar solvent to the polar solvent is 1:0.5 to 2;

an amount of the solvent is 5 to 20 times the weight of the compound (a).

In some embodiments of the present invention, the compound (c) can be prepared by reacting the compound (b) with an acid, wherein, the acid is preferably an inorganic acid or an organic acid;

the inorganic acid is preferably hydrochloric acid, sulfuric acid or nitric acid;

the organic acid is preferably trifluoroacetic acid, methanesulfonic acid and/or p-toluenesulfonic acid;

a molar ratio of the compound (b) to the acid is 1:5 to 30;

the reaction is carried out in a solvent, the solvent is preferably water or an organic solvent;

the organic solvent is preferably ethyl acetate, methanol and/or dioxane;

an amount of the solvent is 5 to 20 times the weight of the compound (b);

temperature of the reaction is 0 to 50° C., preferably 10 to 30° C.;

the reaction time is 2 to 30 hours, preferably 2 to 8 hours.

In some embodiments of the present invention, the compound (d) can be prepared by reacting the compound (c) with a hydrogenation reducing agent/system, wherein, the hydrogenation reducing agent/system is preferably a heavy metal catalyzing hydrogenation system and reducing metal;

the heavy metal catalyzing hydrogenation system is preferably using dry palladium on carbon, wet palladium on carbon, Raney nickel or palladium hydroxide as a catalyst, hydrogen gas as a reducing agent;

the reducing metal is preferably iron or zinc powder;

the weight ratio of the compound (c) to the heavy metal is preferably 100: (2 to 30);

the reaction is carried out in a solvent, the solvent is preferably a single organic solvent or a mixed organic solvent;

the organic solvent is preferably ethyl acetate, methanol, ethanol, tetrahydrofuran and/or DMF;

an amount of the solvent is 5 to 200 times the weight of the compound (d);

temperature of the reaction is 0 to 50° C., preferably 20 to 40° C.;

the reaction time is 2 to 30 hours; preferably 8 to 16 hours.

In some embodiments of the present invention, the compound (IV) can be prepared by reacting the compound (d) with a common amino-protecting agent in the presence of a base;

the amino-protecting agent is preferably selected from an alkoxycarbonyl amino-protecting agent;

the amino-protecting agent is selected from CbzCl, (Boc)$_2$O, 2-(tert-butoxycarbonyloxyimino)-2-phenylacetonitrile, ethyl chloroformate, methyl chloroformate, Fmoc-Cl, Fmoc N-hydroxysuccinimide ester, allyl chloroformate, N-[2-(trimethylsilyl)ethoxycarbonyloxy] succinimide, and the like.

The base is preferably an alkali metal base, an alkaline earth metal base and an organometallic base;

the alkali metal base is preferably selected from lithium hydroxide, sodium hydroxide, potassium hydroxide, cesium hydroxide, sodium carbonate, potassium carbonate, cesium carbonate, sodium bicarbonate and/or potassium bicarbonate;

the alkaline earth metal base is preferably selected from sodium hydride, potassium hydride and/or calcium hydride;

the organometallic base is selected from sodium methoxide, lithium tert-butoxide, sodium tert-butoxide, potassium tert-butoxide, sodium ethoxide and/or aluminum isopropoxide.

A molar ratio of the compound (d) to the base is preferably 1:1 to 3;

a molar ratio of the compound (d) to the amino-protecting agent is preferably 1:1 to 2;

the reaction is carried out in a solvent, the solvent is preferably a mixed solvent of water and an organic solvent;

the organic solvent is preferably benzene, toluene, dioxane, tetrahydrofuran and/or methyl tetrahydrofuran;

a volume ratio of water to the organic solvent is 1:0.5 to 2;

an amount of the solvent is 5 to 20 times the weight of the compound (d);

temperature of the reaction is −20 to 50° C., preferably −5 to 15° C.;

the reaction time is 2 to 30 hours.

The present invention provides an alternative process for preparing compound (IV) in some embodiments, comprising

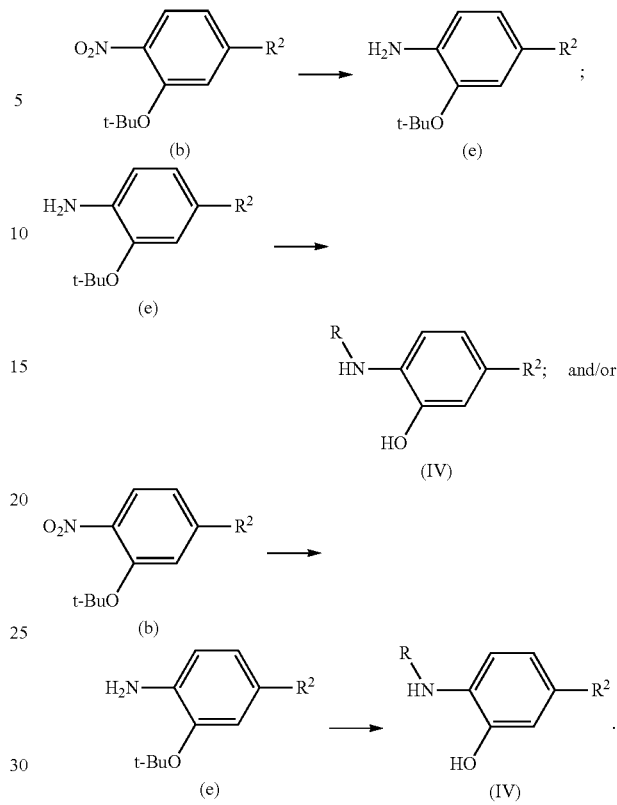

In some embodiments of the present invention, the compound (e) can be prepared by reacting the compound (b) with a hydrogenation reducing agent/system, wherein, the hydrogenation reducing agent/system is preferably a heavy metal catalyzing hydrogenation system and/or reducing metal;

the heavy metal catalyzing hydrogenation system is preferably using dry palladium on carbon, wet palladium on carbon, Raney nickel and/or palladium hydroxide as a catalyst, hydrogen gas as a reducing agent;

the reducing metal is preferably iron or zinc powder;

the weight ratio of the compound (b) to the heavy metal is preferably 100:2 to 30;

the reaction is carried out in a solvent, the solvent is preferably a single organic solvent or a mixed organic solvent;

the organic solvent is preferably ethyl acetate, methanol, ethanol, tetrahydrofuran and/or DMF;

an amount of the solvent is 5 to 200 times the weight of the compound (b);

temperature of the reaction is 0 to 50° C., preferably 20 to 40° C.;

the reaction time is 2 to 30 hours; preferably 4 to 8 hours.

In some embodiments of the present invention, the process for preparing the compound (IV) by reacting the compound (e) with an amino-protecting agent can refer to the process for preparing the compound (IV) with the compound (d).

The present invention also provides two stable crystal forms of the compound 1, crystal form A and crystal form B, which have promising prospects for a medical use, the structures of which are shown as FIG. 1 and FIG. 2.

The invention also provides a process for preparing crystal form A and crystal form B of the compound 1, comprising adding any one of the forms of the compound 1 to a solvent, crystallizing, and producing different forms of crystal, wherein, the solvent is preferably an organic solvent or a mixed solvent containing an alcohol solvent or water;

the organic solvent is preferably an alcohol or a ketone;

the alcohol is preferably methanol, ethanol, isopropanol and/or n-butanol;

the ketone is preferably acetone and/or methyl ethyl ketone;

the mixed solvent is preferably a mixed solvent of DMSO and ethanol or a mixed solvent of DMSO and water;

a volume ratio of DMSO to ethanol or water is 1:0.5 to 5;

an amount of the solvent is 3 to 50 times the weight of the compound 1.

DEFINITION AND DESCRIPTION

Unless indicated otherwise, the following terms and phrases used herein are intended to include the following meanings. A specific phrase or term which is not specifically defined should not be considered to be uncertain or unclear, but should be understood in accordance with the ordinary meaning. When a trade name appears herein, it is intended to refer to its corresponding commodity or its active ingredient.

The intermediates of the present invention may be prepared by a variety of synthetic processes well-known to a person skilled in the art, which include the specific embodiments listed below, their combinations with other chemical synthetic processes, and equivalent alternatives known to a person skilled in the art, and preferred embodiments, include but are not limited to the embodiments of the present invention.

The chemical reaction of a specific embodiment of the present invention is carried out in a suitable solvent, the solvent should be suitable for the chemical changes of the present invention and the reagents and materials required. In order to obtain the compounds of the present invention, it will sometimes be desirable for a person skilled in the art to modify or select a synthesis step or a reaction process on the basis of the present embodiments.

One of the important considerations in any designs of synthetic route in the art is to select suitable protecting groups for reactive functional groups (such as the amino group in the present invention). For trained practitioners, Greene and Wuts (Protective Groups In Organic Synthesis, Wiley and Sons, 1991) are authorities in this regard. All references cited herein are incorporated by reference in their entirety.

The following embodiments further illustrate the present invention, but the present invention is not limited thereto.

All of the solvents used in the present invention are commercially available and can be used without further purification. The reaction is generally carried out under inert nitrogen gas in an anhydrous solvent. Proton nuclear magnetic resonance datas were recorded on a Bruker Avance III 400 (400 MHz) spectrometer with a chemical shift represented by (ppm) at the low field of tetramethylsilane. The mass spectrum was measured on the Agilent 1200 Series plus 6110 (& 1956A). LC/MS or Shimadzu MS contains a DAD: SPD-M20A (LC) and a Shimadzu Micromass 2020 detector. The mass spectrometer is equipped with an electrospray ion source (ESI) operating in a positive/negative mode.

The following abbreviations are used in the present invention: DCM represents dichloromethane; PE represents petroleum ether; EA represents ethyl acetate; Pd/C represents palladium on carbon; DMF represents N,N-dimethyl formamide; DMAC represents N,N-dimethyl acetamide; DMSO represents dimethyl sulfoxide; EtOAc represents ethyl acetate; EtOH represents ethanol; MeOH represents methanol; Cbz represents benzyloxycarbonyl, which is an amine protecting group; Boc represents tert-butylcarbonyl, which is an amine protecting group; Fmoc represents fluorenylmethyloxycarbonyl, which is an amine protecting group; Alloc represents an allyloxycarbonyl, which is an amine protecting group; Teoc represents trimethylsilylethoxy carbonyl, which is an amine protecting group; HOAc represents acetic acid; r.t. represents room temperature; O/N represents overnight; THF represents tetrahydrofuran; $Boc_2O$ represents di-tert-butyl Bicarbonate; TFA represents trifluoroacetic acid; DIPEA represents diisopropylethylamine; DIFA represents diisopropylethylamine; DMAP represents 4-dimethylaminopyridine; DBU represents 1,8-diazabicycloundec-7-ene; tol represents toluene; $NH_4Cl$ represents ammonium chloride; THF represents tetrahydrofuran; i-PrOH represents 2-propanol; mp represents melting point; NMP represents N-methylpyrrolidone; t-BuOK represents potassium tert-butoxide; AcOH represents glacial acetic acid; rf represents reflow; $MeNH_2$ represents methylamine; $Et_3N$ represents triethylamine; $H_2O_2$ represents hydrogen peroxide; Con.HCl (aq) represents aqueous concentrated hydrochloric acid solution.

The compounds are named by hand or ChemDraw® software, names of commercially available compounds refer to the supplier catalogs.

The progresses achieved by the process for synthesizing the compound of formula (I) and the intermediate thereof provided by the present invention are that it overcomes the shortcomings of the processes in the prior art, such as expensive raw materials, high toxic reagents, mean reaction conditions, hard purifications and not suitable to scale up. Specifically, 1) the raw materials used for preparing the compound of formula (I) in the present invention are conventional or common, which are available in the market and low in price;

2) the intermediate compound (II) can be obtained by reacting the novel intermediate compound (IV) with the known intermediate compound (III) by one step, which effectively improves the yield;

3) chiral natural products are used as raw materials to introduce chiral centers so as to give the compounds of formula (I) with high optical purity;

4) the reagents used in each step are small molecules which results in easy purification.

Therefore, the present invention has high industrial application value and economic value regarding the process for preparing the compound of formula (I) and the intermediate thereof.

DETAILED DESCRIPTION OF THE PREFERRED EMBODIMENT

Figure 1:
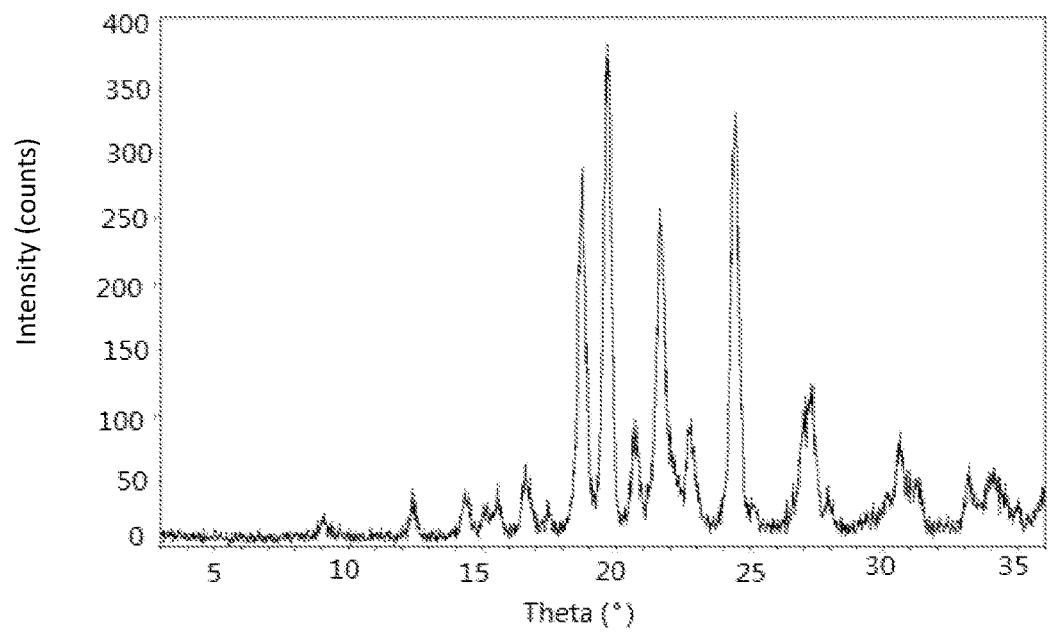
FIG. 1 is the XRPD spectra of crystal form A of the compound 1 under Cu—K alpha radiation, where the crystal form A is obtained by crystallizing the compound 1 in ethanol.
Figure 2:
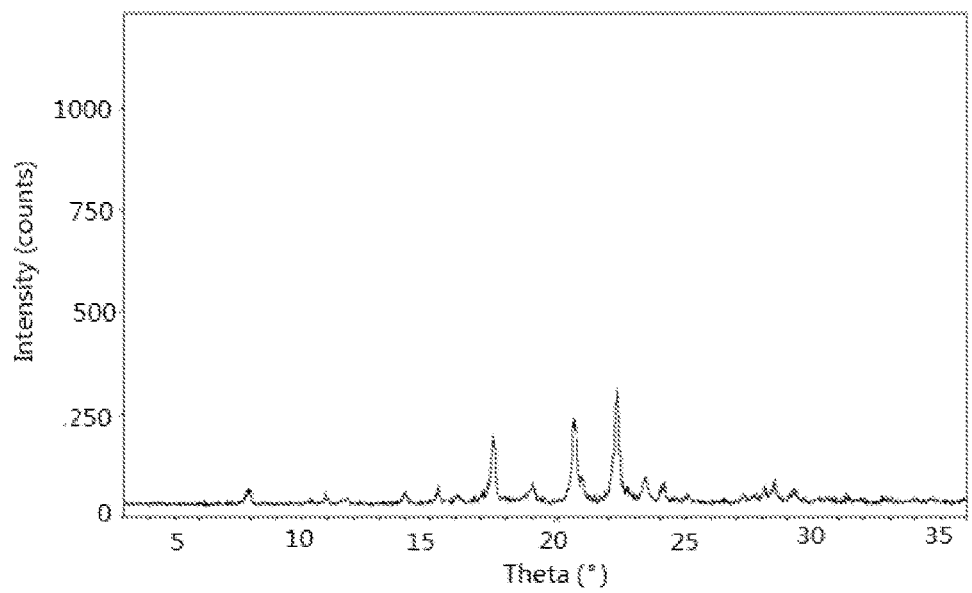
FIG. 2 is the XRPD spectra of crystal form B of the compound 1 under Cu—K alpha radiation, where the crystal form B is obtained by crystallizing the compound 1 in DMSO/EtOH system.
Figure 3:
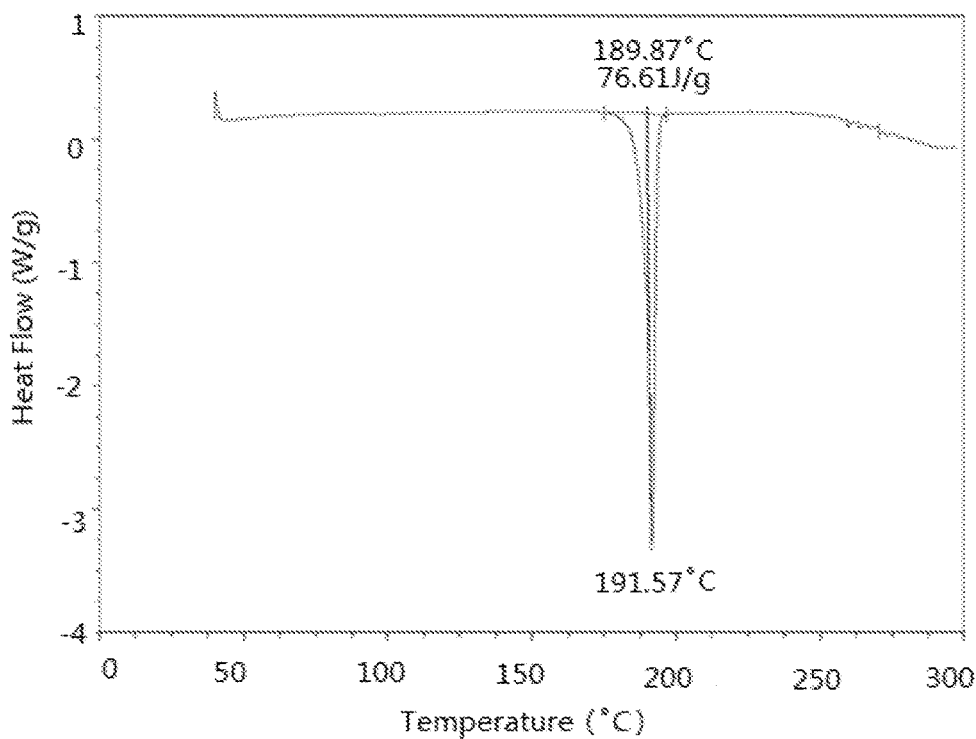
FIG. 3 is a DSC spectrum of crystal form A of the compound 1.
Figure 4:
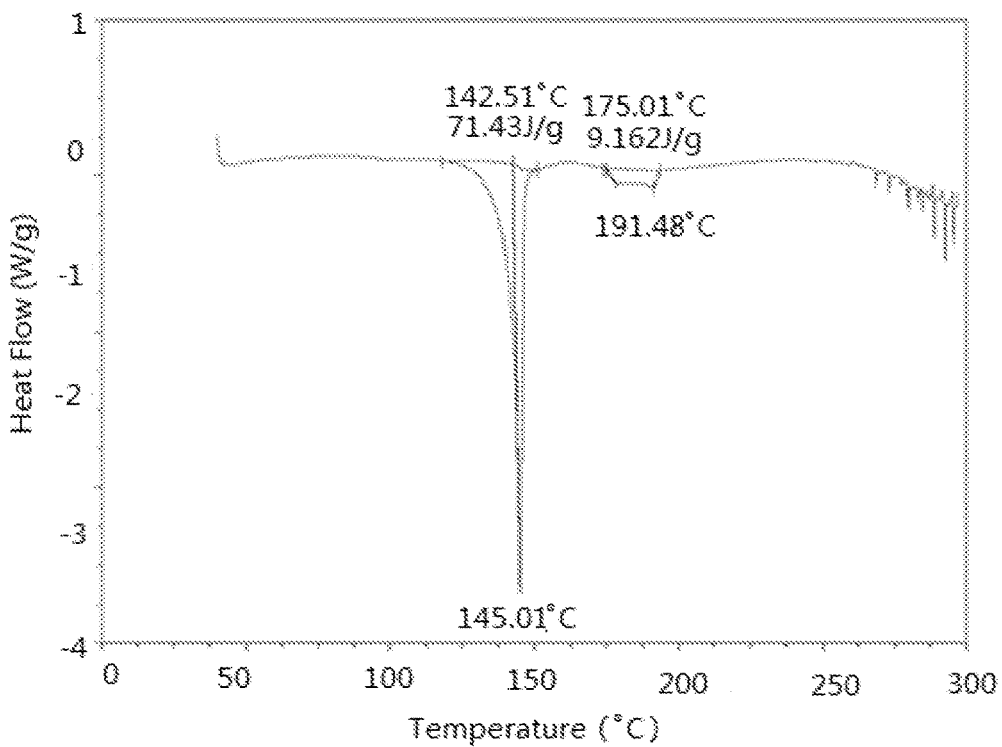
FIG. 4 is a DSC spectrum of crystal form B of the compound 1.

For better understanding the present invention, the following embodiments further illustrate the present invention, but the present invention is not limited thereto.

Embodiment 1 The Process for Preparing the Compound 1

Process 1

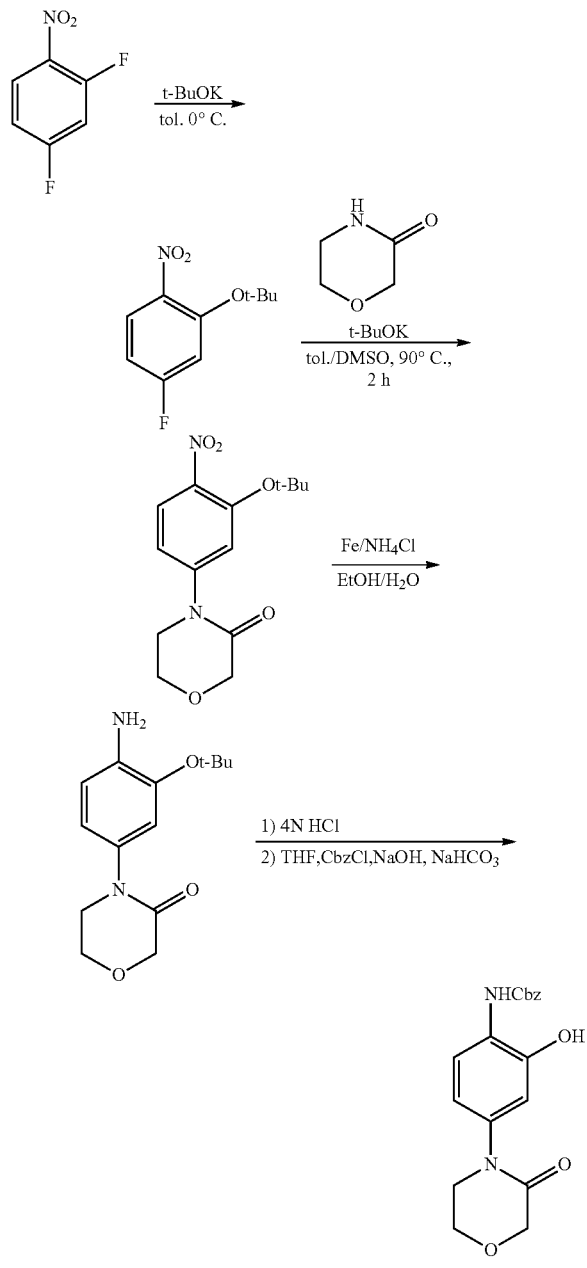

Step 1: Synthesis of 2-(tert-butoxy)-4-fluoro-1-nitrobenzene

Under an ice-water bath, potassium tert-butoxide (387 g, 3.46 mol) was slowly added to a solution of 2,4-difluoronitrobenzene (500 g, 3.14 mol) in toluene (2 L) in batches, the temperature was kept no more than 20° C. After the addition, the reaction solution was cooled to 0° C. and stirred for 2 hours at this temperature. TLC plate (petroleum ether) was used to detect whether the reaction was complete. The reaction solution was poured into a cold saturated ammonium chloride solution (3 L), the mixture was extracted with ethyl acetate (1 L×3). The organic phases were combined and dried to give 2-(tert-butoxy)-4-fluoro-1-nitrobenzene (670 g, crude, dark red oil, HPLC 90%), which was not further purified and used directly in the next step. $^1$HNMR (CDCl$_3$, 400 MHz) δ 7.82 (dd, J=9.2, 6.0 Hz, 1H), 6.93 (dd, J=10.4, 2.8 Hz, 1H), 6.84 (m, 1H), 1.48 (s, 9H).

Step 2: Synthesis of 4-(3-(tert-butoxy)-4-nitrophenyl)morpholin-3-one

Under an ice-water bath, potassium tert-butoxide (315 g, 2.81 mol) was slowly added in batches to a solution of 2-(tert-butoxy)-4-fluoro-1-nitrobenzene (600 g, 2.81 mol) and morpholin-3-one (284 g, 2.81 mol) in a mixed solvent of toluene and dimethyl sulfoxide (1:1, 1 L) while the temperature was kept no more than 20° C. After the addition, the reaction solution was heated to 90° C. and stirred at this temperature for 2 hours. TLC (PE) was used to detect whether the reaction was complete. The reaction solution was poured into a cold saturated ammonium chloride solution (4 L), the mixture was extracted with ethyl acetate (1 L×2). The combined organic phase was washed with water (2 L) and evaporated to give 4-(3-(tert-butoxy)-4-nitrophenyl)morpholin-3-one (828 g, crude, dark red oil, HPLC 80%), which was not further purified and used directly in the next step. $^1$HNMR (CDCl$_3$, 400 MHz) δ 7.79 (d, J=9.2 Hz, 1H), 7.42 (d, J=2.0 Hz, 1H), 7.10 (dd. J=8.8, 2.4 Hz, 1H), 4.36 (s, 2H), 4.06 (t, J=2.0 Hz, 2H), 3.82 (t, J=2.0 Hz, 2H), 1.45 (s, 9H).

Step 3: Synthesis of 4-(4-amino-3-(tert-butoxy)phenyl)morpholin-3-one

Iron powder (106 g, 1.90 mol) was added to a vigorously stirred mixed solution of 4-(3-(tert-butoxy)-4-nitrophenyl)morpholin-3-one (140 g, 0.475 mol) and ammonium chloride (101 g, 1.90 mol) in ethanol and water (3:1, 1.2 L). After the addition, the reaction was stirred for about half an hour and became greatly exothermic, cooled with ice water until the heat release stopped, and then warmed to room temperature overnight. TLC (PE:EA=1:1) was used to detect whether the reaction was complete, filtered, and the residue was washed with methanol. TLC (PE:EA=1:1) was used to detect the wash was complete. The filtrates were combined and evaporated to dry, washed with water (500 mL) and extracted with dichloromethane (300 mL×3). The organic phases were combined and dried to give 4-(4-amino-3-(tert-butoxy)phenyl)morpholin-3-one (125 g, crude, black oil, HPLC 70%), which was not further purified and used directly in the next step. $^1$HNMR (CDCl$_3$, 400 MHz) δ 6.84 (d, J=2.0 Hz, 1H), 6.75 (m, 1H), 6.65 (m, 1H), 4.76 (brs, 2H), 4.14 (s, 2H), 3.91 (t, J=2.0 Hz, 2H), 3.62 (t, 2.0 Hz, 2H), 1.33 (s, 9H).

Step 4: Synthesis of benzyl (2-hydroxyl-4-(3-ketomorpholine)phenyl) carbamate 4-(4-amino-3-(tert-butoxy)phenyl)morpholin-3-one (400 g, 1.51 mol) was dissolved in 4N hydrochloric acid solution (1 L), stirred and reacted overnight. The reaction solution was cooled with ice water, and the pH value of the reaction solution was adjusted to about 7 with 12N sodium hydroxide solution, and then sodium bicarbonate solid (190 g, 2.23 mol) and tetrahydrofuran (600 mL) were added. After cooling to 0° C., a solution of benzyl chloroformate (258 g, 1.51 mol) in tetrahydrofuran (500 mL) was slowly added dropwise and the temperature was kept below 10° C. After the addition, TLC (PE:EA=1:3) was used to detect the reaction was complete. Dichloromethane (2 L) and water (1 L) were added to the reaction solution, layered and the aqueous phase was extracted with dichloromethane (1 L×2). The organic phases were combined and evaporated to dry, and then the ethanol was added to triturate, filtered, the filter cake was washed twice with ethanol (200 mL), the cake was then dried to give benzyl (2-hydroxyl-4-(3-ketomorpholine)phenyl)carbamate (225 g, HPLC 98%), brown solid. $^1$HNMR (DMSO-$d_6$, 400 MHz) δ 9.95 (brs, 1H), 8.52 (s, 1H), 7.56 (d, J=9.2 Hz, 1H), 7.45-7.33 (m, 5H), 6.91 (d, J=2.4 Hz, 1H), 6.79 (dd, J=8.4, 2.0 Hz, 1H), 5.15 (s, 2H), 4.18 (s, 2H), 3.95 (t, J=4.8 Hz, 2H), 3.66 (t, J=4.8 Hz, 2H), 1.33 (s, 9H).

Process 2

Step 5: Synthesis of 4-(3-(hydroxyl)-4-nitrophenyl)morpholin-3-one 10 mL Con. HCl (aq) was slowly added to a solution of 4-(3-(tert-butoxy)-4-nitrophenyl)morpholin-3-one (10.0 g, 34.0 mmol) in ethyl acetate (30 mL). After the mixture was stirred at room temperature overnight, water (50 mL) was added and the mixture was extracted with ethyl acetate (30 mL×2). The organic phases were combined and evaporated to dry to give a crude, and then ethanol (100 mL) was added to triturate, filtered and evaporated to dry to give 4-(3-(hydroxyl)-4-nitrophenyl)morpholin-3-one (4.12 g, HPLC 98%, yield 51%). $^1$HNMR (DMSO-$d_6$, 400 MHz) δ 11.1 (brs, 1H), 7.96 (d, J=8.0 Hz, 1H), 7.31 (d, J=2.4 Hz, 1H), 7.11 (dd, J=8.8, 2.4 Hz, 1H), 4.25 (s, 2H), 3.98 (t, J=4.8 Hz, 2H), 3.79 (t, J=4.8 Hz, 2H), 1.33 (s, 9H).

Step 6: Synthesis of 4-(4-amino-3-(hydroxyl)phenyl)morpholin-3-one

In a 250 mL hydrogenation flask, under nitrogen gas protection, dry palladium on carbon (200 mg) was added to a solution of 4-(3-(hydroxyl)-4-nitrophenyl)morpholin-3-one (3.5 g, 14.7 mmol) in methanol (100 mL). The reaction solution was stirred at 30° C. for 16 hours at 30 psi hydrogen pressure. TLC (PE:EA=1:1) was used to detect the reaction was complete, and the mixture was filtered, the filter cake was washed with hot methanol (200 mL). The combined organic phase was evaporated to dry to give 4-(4-amino-3-(hydroxyl)phenyl)morpholin-3-one (2.7 g, HPLC 91%, yield 88%). $^1$HNMR (DMSO-$d_6$, 400 MHz) δ 9.22 (brs, 1H), 6.63 (s, 1H), 6.57 (d, J=8.4 Hz, 1H), 6.51 (d, J=8.4 Hz, 1H), 4.59 (brs, 2H), 4.13 (s, 2H), 3.91 (t, J=4.4 Hz, 2H), 3.57 (t, J=4.4 Hz, 2H).

Step 7: Synthesis of benzyl (2-hydroxyl-4-(3-ketomorpholine)phenyl) carbamate Under an ice-water bath, sodium bicarbonate solid (1.63 g, 1.9.4 mmol) was added to a mixed solution of 4-(4-amino-3-(hydroxyl)phenyl)morpholin-3-one (2.7 g, 12.9 mmol) in tetrahydrofuran (10 ml) and water (15 mL). After cooling to 0° C., a solution of benzyl chloroformate (1.63 g, 19.4 mmol) in tetrahydrofuran (5 ml) was slowly added dropwise and the temperature was kept no more than 5° C. After the addition, TLC (PE:EA=1:3) was used to detect the reaction was complete. Water (30 ml) was added to the reaction solution and stirred for five minutes and then filtered, the filter cake was washed with water (10 ml), collected and evaporated to dry, triturated with ethanol to give benzyl (2-hydroxyl-4-(3-ketomorpholine)carbamate (3.66 g, white solid, HPLC 96%, yield 82%). $^1$HNMR (DMSO-$d_6$, 400 MHz) δ 9.95 (brs, 1H), 8.52 (s, 1H), 7.56 (d, J=9.2 Hz, 1H), 7.45-7.33 (m, 5H), 6.91 (d, J=2.4 Hz, 1H), 6.79 (dd, J=8.4, 2.0 Hz, 1H), 5.15 (s, 2H), 4.18 (s, 2H), 3.95 (t, J=4.8 Hz, 2H), 3.66 (t, J=4.8 Hz, 2H), 1.33 (s, 9H).

Process 3

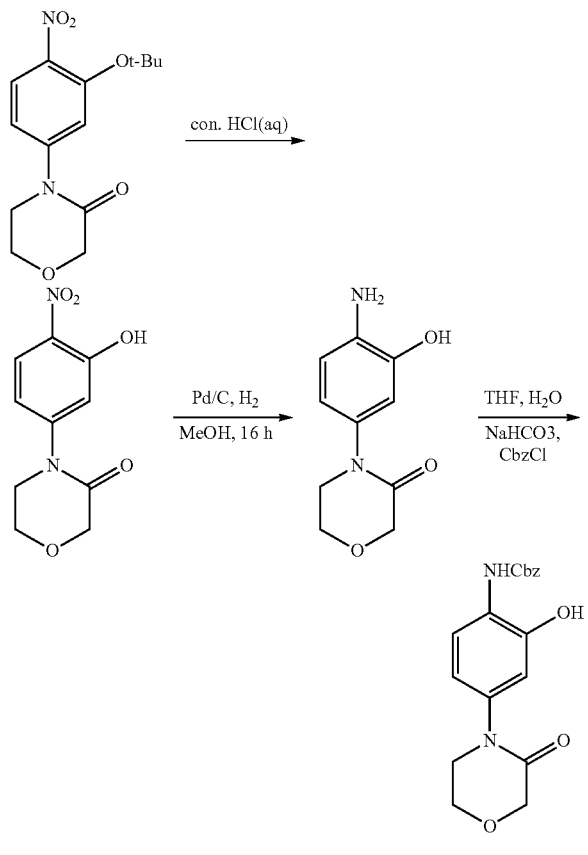

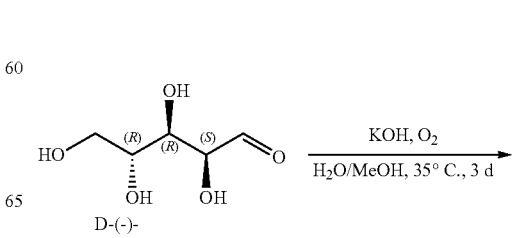

-continued

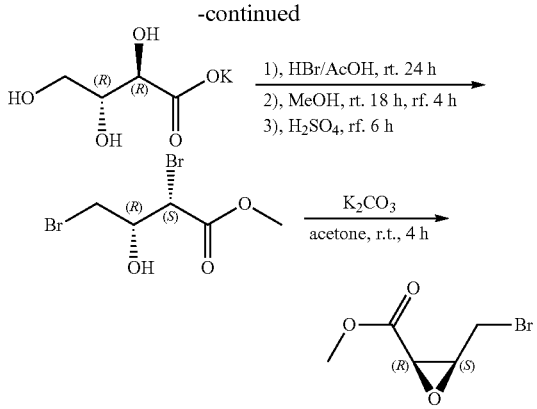

Step 8: Synthesis of potassium (2R,3R)-2,3,4-trihydroxyl butyrate

Under an ice-water bath, potassium hydroxide (1.12 kg, 19.98 mol) was slowly added to a mixed solvent of methanol (10 L) and water (2.4 L) and the temperature was kept no more than 45° C. After the addition, oxygen gas was introduced into the reaction solution, when the reaction solution was cooled to 35° C., an aqueous solution of D-(−)-arabinose (1 kg, 6.66 mol, dissolved in 2.4 L water) was added dropwise over more than 6 hours (oxygen gas was introduced during the whole period) and the reaction temperature was kept at 35° C. After the addition, oxygen gas was further introduced for 2 hours, followed by introducing air for 60 hours. The reaction solution was concentrated under reduced pressure to give 2.4 L oil and the oil was slowly added dropwise into the rapidly stirring methanol (IOL) and a large amount of white solid was precipitated. After the addition, the mixture was filtered and dried in vacuum to give white solid (560 g, yield 48%). $^1$HNMR (D$_2$O, 400 MHz) δ 4.09 (d, J=4.0 Hz, 1H), 3.97-3.92 (m, 1H), 3.65 (d, J=5.6 Hz, 1H).

Step 9: Synthesis of methyl (2S,3R)-2,4-dibromo-3-hydroxylbutyrate

A solution of hydrogen bromide/acetic acid (33%, 2 L) was added to a reactor containing potassium (2R,3R)-2,3,4-trihydroxylbutyrate (560 g, 3.21 mol). The mixture was stirred at room temperature for 24 hours, and then poured into anhydrous methanol (14 L) and further stirred at room temperature for 18 hours. The reaction solution was heated to 65° C. and refluxed for 4 hours and then concentrated under reduced pressure. Water (1 L) and ethyl acetate (1.5 L) were added to extract, the organic phase was separated, dried over sodium sulfate, concentrated to give a mixture of (2S,3R)-2,4-dibromo-3-hydroxylbutyric acid and methyl (2S,3R)-2,4-dibromo-3-hydroxylbutyrate as an oil (706 g). Sulfuric acid (60 mL) was slowly added to a solution of the mixture (680 g) in methanol (3.5 L), heated to reflux for 6 hours. TLC (PE:EA=10:1) was used to detect the reaction was complete, the reaction solution was concentrated, the residue was dissolved in ethyl acetate (800 ml), washed with water (500 ml), the organic phase was dried over anhydrous sodium sulfate, filtered and concentrated to give the product as an off-white solid (650 g, yield 74%). $^1$HNMR (CDCl$_3$, 400 MHz) δ 4.71 (d, J=3.6 Hz, 1H), 4.20-4.15 (m, 1H), 3.83 (s, 3H), 3.55-3.48 (m, 2H).

Step 10: Synthesis of methyl (2R,3S)-3-bromomethyl ethylene oxide-2-carboxylate Potassium carbonate (503 g, 3.65 mol) was added to a solution of methyl (2S,3R)-2,4-dibromo-3-hydroxylbutyrate (200 g, 0.729 mol) in acetone (2.5 L), the reaction was carried out at room temperature for 4 hours, TLC (PE: EA=10:1) showed that the raw material disappeared. The reaction solution was filtered and concentrated under reduced pressure to give the product as a pale yellow oil, which was distilled to give the product as a colorless liquid (126 g, 90%) by using a vacuum distillation apparatus. $^1$HNMR (CDCl$_3$, 400 MHz) δ 3.83 (s, 3H), 3.67-3.62 (m, 2H), 3.57-3.52 (m, 1H), 3.46-3.43 (m, 1H).

Process 4

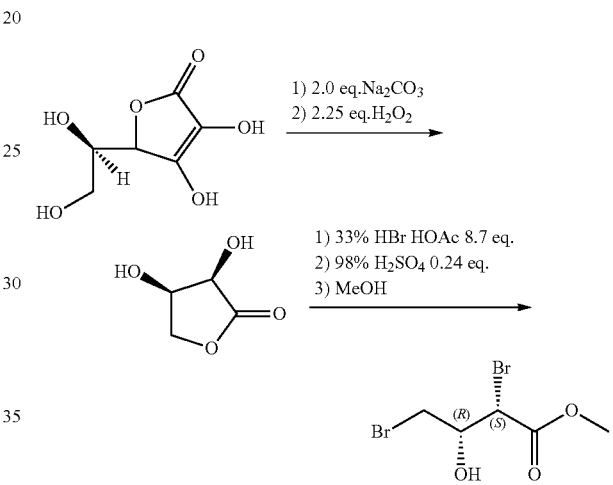

Step 11: Synthesis of (3R,4R)-3,4-dihydroxyl dihydrofuran-2(3H)-one

The isoascorbic acid (17.6 g, 0.1 mol) was dissolved in 250 mL water and the mixture was cooled to 0 to 6° C. Anhydrous sodium carbonate powder (21.2 g, 0.2 mol) was added to the reaction flask in batches. After the addition, 30% hydrogen peroxide (22 mL) was added while stirring, and the internal temperature was raised from 6° C. to 19° C. The mixture was further stirred for 5 minutes under an ice bath and the internal temperature was raised to 27° C. The reaction solution was heated to 42° C. and stirred for 30 minutes. The zinc powder (1.0 g, 0.015 mol) was added to the reaction solution to quench the excess hydrogen peroxide, starch potassium iodide test paper showed negative result. The pH value of the reaction solution was adjusted to 1.0 with 6N hydrochloric acid. The mixture was concentrated at 50° C. under reduced pressure until little amount of white solid was precipitated. Extracted with ethyl acetate (150 ml×3). The organic phase was concentrated to 200 mL (10 to 15 vol); the temperature was cooled to 15 to 25° C. and the mixture was stirred for 5 to 8 hours, (a large amount of white solid precipitated) filtered and dried to give 8.26 g (3R,4R)-3,4-dihydroxyl dihydrofuran-2(3H)-one, yield 70%. $^1$HNMR (DMSO-d$_6$, 400 MHz) δ 5.78 (brs, 1H), 5.37 (brs, 1H), 4.39 (d, J=4.4 Hz, 1H), 4.30-4.22 (m, 2H), 4.05 (d, J=10.0 Hz, 1H).

Step 12: Synthesis of methyl (2S,3R)-2,4-dibromo-3-hydroxylbutyrate (3R,4R)-3,4-dihydroxyldihydrofuran-2(3H)-one (26.0 g, 221 mmol) and 182.0 mL 33% hydrobromic acid in acetic acid were added to a 1 L flask. After the mixture was stirred at room temperature for 24 hours, 959.0 mL methanol was added and the mixture was further stirred for 36 hours. The resulting reaction solution was heated to 65 to 75° C. and refluxed for 4 hours. The reaction solution was concentrated under reduced pressure, water (70.0 mL) and ethyl acetate (105.0 mL) were added and extracted. The organic phase was separated, dried over sodium sulfate, concentrated to give 51 g crude oil mixture. Sulfuric acid (4.1 mL) was added slowly into a solution of the mixture (51.0 g) in methanol (239.0 mL), the mixture was heated to reflux for 6 hours (60 to 70° C.). The reaction solution was concentrated, the residue was dissolved in ethyl acetate (60.0 mL), washed with water (30 mL). The organic phase was dried over anhydrous sodium sulfate, filtered to give the product as white-off solid (51 g, yield 83%). $^1$HNMR (D$_2$O, 400 MHz) δ 3.98 (d, J=4.0 Hz, 1H), 3.86-3.81 (m, 2H), 3.54-3.51 (m, 2H).

Process 5

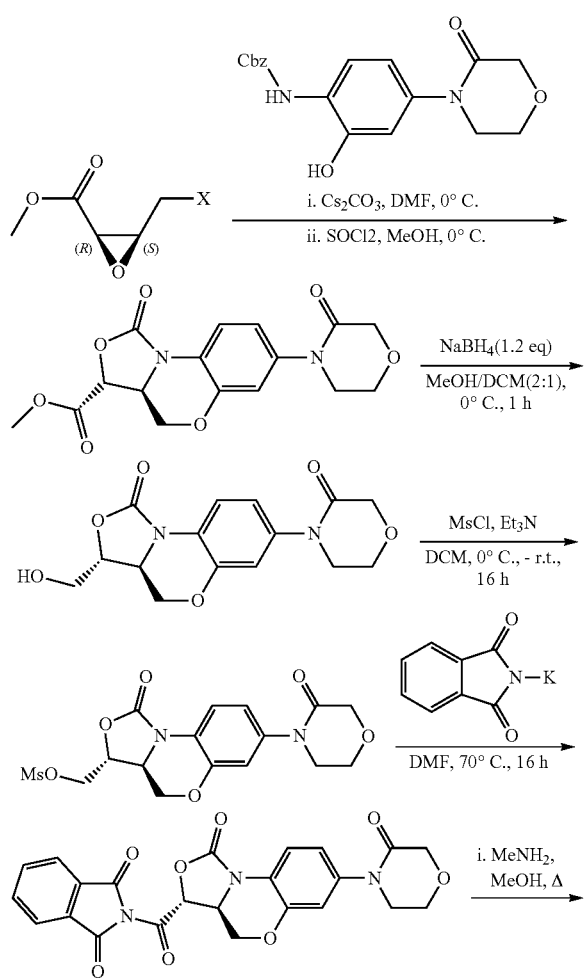

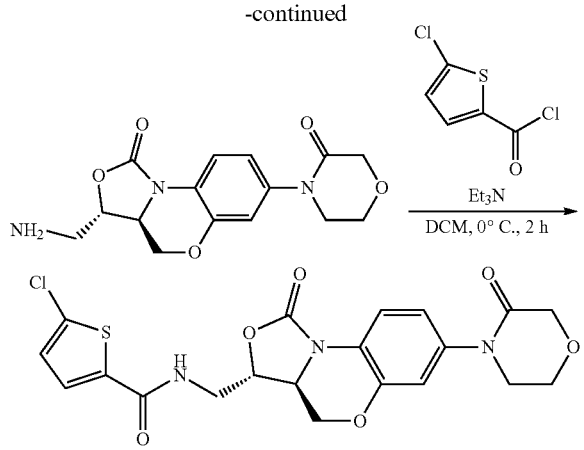

Step 13: Synthesis of (3R,3aS)-methyl-1-one-7-(3-ketomorpholine)-1,3,3a,4-tetrahydrobenzo[b]oxazolo[3,4-d][1,4]oxazine-3-carboxylic acid At 0° C., methyl (2S,3R)-2,4-dibromo-3-hydroxylbutyrate (46.8 g, 0.24 mol), cesium carbonate (130.3 g, 0.40 mol) were added sequentially at one time to a solution of benzyl (2-hydroxyl-4-(3-ketomorpholine)phenyl)carbamate (68.5 g, 0.20 mol) in DMF (700 mL) while stirring. The reaction solution was stirred at 0° C. for 10 hours. Cesium carbonate (65.2 g, 0.20 mol) was further added at 0° C. after the detection result showed (2-hydroxyl-4-(3-ketomorpholine)phenyl)carbamate completely disappeared. The reaction solution was gradually warmed to room temperature and stirred for 12 hours. The reaction mixture was cooled to 0° C., methanol (700 mL) was added and the pH value was adjusted to 1 with 4 N HCl/methanol solution. Sulfoxide chloride (58 mL, 0.80 mol) was slowly added dropwise over about 1 hour at 0° C. The reaction was further stirred at 0° C. for 1 hour and then gradually warmed to room temperature and reacted for 16 hours. When the detection result showed the reaction was complete, the reaction solution was concentrated under reduced pressure at 40° C. to remove methanol. The resulting reaction mixture was cooled and added to a cold aqueous hydrochloric acid solution whose pH value was 2. Solid was collected after filtration to give the crude product and the crude product was washed twice with cold aqueous hydrochloric acid solution (40 mL, pH=2) and twice with methanol (40 mL), and then dried in vacuum to give the target product as a white solid (38 g, yield 54%). $^1$HNMR (DMSO-d$_6$, 400 MHz) δ 7.81 (d, J=8.4 Hz, 1H), 7.08-7.02 (m, 2H), 5.15 (d, J=6.8 Hz, 1H), 4.58 (d, J=9.2, 3.2 Hz, 1H), 4.40 (m, 1H), 4.18 (s, 2H), 4.15 (m, 1H), 3.95 (t, J=4.4 Hz, 1H), 3.80 (s, 2H), 3.69 (t, J=4.4 Hz, 1H).

Step 14: Synthesis of (3R,3aS)-3-(hydroxylmethyl)-7-(3-ketomorpholine)-3a,4-dihydrobenzo[b]oxazolo[3,4-d][1,4]oxazin-1(3H)-one At 0° C., sodium borohydride (5.0 g, 0.13 mol) was added to a suspension of (3R,3aS)-methyl-1-one-7-(3-ketomorpholine)-1,3,3a,4-tetrahydrobenzo[b]oxazolo[3,4-d][1,4]oxazine-3-carboxylic acid (38.3 g, 0.11 mol) in methanol/dichloromethane (660 mL, 2:1) in batches while stirring over about 40 minutes. The reaction was stirred at 0° C. for 20 minutes. The reaction solution was warmed to room temperature, and the solvent was removed under reduced pressure at 40° C. to obtain a crude. The crude was triturated in water (40 mL) for 10 minutes, filtered, washed with water (20 mL) once and dried in vacuum to give the desired product 28 g. The aqueous phase was extracted with methanol/dichloromethane (1:10), dried over anhydrous sodium sulfate and concentrated to give 5 g the desired product, total yield 90%. $^1$HNMR (DMSO-$d_6$, 400 MHz) δ 7.84 (d, J=8.8 Hz, 1H), 7.05-6.99 (m, 2H), 5.34 (brs, 1H), 4.54 (d, J=7.2 Hz, 1H), 4.45 (m, 1H), 4.18 (s, 2H), 4.02 (t, J=4.4 Hz, 1H), 3.95 (s, 2H), 3.77-3.68 (m, 4H).

Step 15: Synthesis of methyl (3R,3aS)-1-one-7-(3-ketomorpholine)-1,3,3a,4-tetrahydrobenzo[b]oxazolo[3,4-d][1,4]oxazin-3-yl)methanesulfonate At 0° C., triethylamine (25 mL, 180 mmol) was added in one portion and methanesulfonyl chloride (9 mL, 120 mmol) was added dropwise over about 20 minutes to a suspension of (3R,3aS)-3-(hydroxylmethyl)-7-(3-ketomorpholine)-3a,4-dihydrobenzo[b]oxazolo[3,4-d][1,4]oxazin-1(3H)-one (19.2 g, 60 mmol) in dichloromethane (600 mL) while stirring. The reaction was stirred at 0° C. for 1 hour and gradually warmed to room temperature and reacted for 16 hours. When the detection showed the reaction was substantially complete, saturated sodium bicarbonate solution (200 mL) was added. The mixture was filtered and the filtrate was portionated. The aqueous phase was extracted with dichloromethane (100 mL×2). The organic phases were combined, washed twice with saturated brine (200 mL), dried over anhydrous sodium sulfate, and combined with the solid after concentration to give the target product (21 g, yield 87%). $^1$HNMR (DMSO-$d_6$, 400 MHz) δ 7.84 (d, J=8.4 Hz, 1H), 7.07-7.01 (m, 2H), 4.79 (m, 1H), 4.64-4.58 (m, 3H), 4.18 (s, 2H), 4.07 (d, J=5.6 Hz, 2H), 3.95 (t, J=4.8 Hz, 1H), 3.69 (t, J=4.8 Hz, 2H), 3.28 (s, 2H).

Step 16: Synthesis of 2-(((3S,3aS)-1-one-7-(3-ketomorpholine)-1,3,3a,4-tetrahydrobenzo[b]oxazolo[3,4-d][1,4]oxazin-3-yl)methyl)isoindole-1,3-dione Methyl ((3R,3aS)-1-one-7-(3-ketomorpholine)-1,3,3a,4-tetrahydrobenzo[b] oxazolo[3,4-d][1,4]oxazin-3-yl)methanesulfonate (5.4 g, 13.5 mmol) was dissolved in DMF (55 mL). At 25° C., potassium phthalimide (3.75 g, 20.3 mmol) was added in one portion while stirring, the mixture was further stirred for 10 minutes and then heated to 70° C. and reacted for 16 hours. When the detection result showed the reaction was substantially complete, the mixture was cooled to room temperature and added to ice water (1.80 mL). The solid was filtered out and collected to give the crude, the crude was washed twice with ice water (20 mL) and dried to give the target product as a white solid (5.4 g, yield 90%). $^1$HNMR (DMSO-$d_6$, 400 MHz) δ 7.95-7.85 (m, 4H), 7.80 (d, J=8.8 Hz, 1H), 7.04 (d, J=2.4 Hz, 1H), 7.00 (dd, J=8.8, 2.4 Hz, 1H), 4.73 (m, 1H), 4.72 (m, 1H), 4.18-4.03 (m, 6H), 3.94 (t, J=4.8 Hz, 1H), 3.68 (t, J=4.8 Hz, 1H).

Step 17: Synthesis of (3S,3aS)-3-(aminomethyl)-7-(3-ketomorpholine))-3a,4-dihydrobenzo[b]oxazolo[3,4-d][1,4]-oxazin-1(3H)-one MeOH (100 mL) was added to a 250 mL reaction flask, followed by the addition of the compound 2-(((3S,3aS)-1-one-7-(3-ketomorpholine)-1,3,3a,4-tetrahydrobenzo[b]oxazolo[3,4-d][1,4]oxazin-3-yl)methyl)isoindole-1,3-dione (10.11 g, 22.5 mmol). After the mixture was fully stirred, a 40% aqueous solution of methylamine (10.5 mL, 135 mmol) was added in one portion, the mixture was further stirred for 10 minutes, and then the temperature was raised to 65° C., further stirred for 4 hours. When the detection result showed the raw material was fully reacted. The reaction solution was then cooled to room temperature and the pH value of which was adjusted to 1 with HCl-MeOH solution (12 mL, 12M) and stirred for 1 hour to form the salt. The reaction solution was concentrated at 40° C. to remove part of methanol (about 50 mL) thereby obtaining a slurry. Followed by the addition of methanol/dichloromethane (60 mL, 1:5) and the mixture was triturated for 16 hours, filtered, the filter cake was washed twice with MeOH (10 mL) and dried to give the hydrochloride salt of the target product (white solid, 7.0 g, yield 87%, purity 98%). $^1$HNMR (DMSO-$d_6$, 400 MHz) δ 7.85 (d, J=8.4 Hz, 1H), 6.98-6.95 (m, 2H), 4.82 (m, 1H), 4.59 (d, J=10.4 Hz, 1H), 4.29 (s, 2H), 4.12-4.01 (m, 4H), 3.71 (t, J=5.6 Hz, 1H), 3.52-3.47 (m, 2H), 3.28 (s, 1H).

Step 18: Synthesis of 5-chloro-N-(((3S,3aS)-1-one-7-(3-ketomorpholine)-1,3,3a,4-tetrahydrobenzo[b]oxazolo[3,4-d][1,4]oxazin-3-yl)methyl)thiophene-2-carboxamide Water (30 mL) and acetone (54 mL) were added to a 250 mL reaction flask, followed by an addition of sodium carbonate (2.48 g, 23.4 mmol), dissolved completely after fully stirred, the mixture was cooled to 0-5° C., (3S,3aS)-3-(aminomethyl)-7-(3-ketomorpholine))-3a,4-dihydrobenzo[b]oxazolo[3,4-d][1,4]oxazin-1(3R)-one hydrochloride (6.40 g, 18.0 mmol) was added over about 10 minutes. At 0 to 5° C., keep stirring until the mixture was completely dissolved (about 30 minutes). And then a solution of 5-chlorothiophene-2-carbonyl chloride (3.90 g, 21.6 mmol) in toluene (11 mL) was added dropwise over about 20 minutes at 0-5° C. After the addition, the reaction was reacted at 0-5° C. for 0.5 hour, then gradually warmed to 20° C. and reacted for 1 hour. During this period, solid was gradually precipitated. TLC (DCM:MeOH=20:1) detected the reaction was complete. Water (100 mL) was added to the reaction solution and stirred for 20 minutes. The mixture was concentrated at 45° C. and the solvent was removed, filtered, and the solid was collected, washed with water (50 ml) and dried to give the target product (white solid, 8.40 g, yield 99%, HPLC 94%, chiral purity 99%). NMR (400 MHz, DMSO-$d_6$) δ 9.00 (t, J=5.6 Hz, 1H), 7.85 (d, J=8.8 Hz, 1H), 7.71 (d, J=4.0 Hz, 1H), 7.21 (d, J=4.0 Hz, 1H), 7.05 (d, J=2.0 Hz, 1H), 7.05 (dd, J=8.8, 2.0 Hz, 1H), 4.62-4.51 (m, 2H), 4.18 (s, 2H), 4.11-4.01 (m, 2H), 3.95 (t, J=5.2 Hz, 2H), 3.73 (t, J=5.2 Hz, 2H), 3.68 (t, J=5.2 Hz, 2H).

Step 19: Recrystallization of 5-chloro-N-(((3S,3aS)-1-one-7-(3-ketomorpholine)-1,3,3a,4-tetrahydrobenzo[b]oxazolo[3,4-d][1,4]oxazin-3-yl)methyl)thiophene-2-carboxamide (Crystal Form A)

2.8 g Crude solid obtained in step 18 was heated to 70° C. and stirred for 30 minutes in 90 mL ethanol, then the mixture was cooled to room temperature and stirred for 16 hours, filtered and 2.4 g solid was collected, HPLC 98.3%, yield 86%.

Step 20: Recrystallization of 5-chloro-N-(((3S,3aS)-1-one-7-(3-ketomorpholine)-1,3,3a,4-tetrahydrobenzo[b]oxazolo[3,4-d][1,4]oxazin-3-yl)methyl)thiophene-2-carboxamide (Crystal Form B)

500 mg Solid of the crude solid achieved in step 18 was dissolved in 0.65 mL DMSO, followed by adding 1.3 mL EtOH, the mixture was heated to 80° C. and fully dissolved, and then naturally cooled to 0 to 10° C. A large amount of solid was precipitated and 400 mg solid was collected after filtration, HPLC 99.3%, yield 80%.

Embodiment 2 The Process for Preparing Compound 2

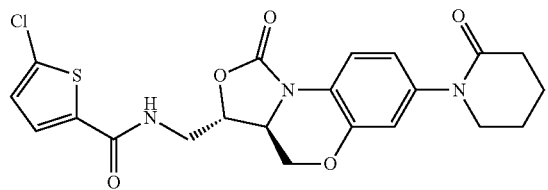 [SMILES: O=C(NC[C@@H]1OC(=O)N2c3ccc(N4CCCCC4=O)cc3OC[C@@H]12)c1ccc(Cl)s1]

The process for preparing compound 2 referred to the process in embodiment 1, where the morpholin-3-one in step 2 was replaced with piperidin-2-one. $^1$H NMR (400 MHz, DMSO-$d_6$) δ 9.01 (t, J=5.6 Hz, 1H), 7.83 (d, J=8.8 Hz, 1H), 7.72 (d, J=4.0 Hz, 1H), 7.22 (d, J=4.0 Hz, 1H), 6.87-6.93 (m, 2H), 4.50-4.64 (m, 2H), 3.99-4.13 (m, 2H), 3.73 (t, J=5.6 Hz, 2H), 3.52-3.60 (m, 2H), 2.37 (t, J=6.0 Hz, 2H), 1.77-1.90 (m, 4H); LCMS (ESI) m/z: 462.1 (M+1).

Embodiment 3 The Process for Preparing Compound 7

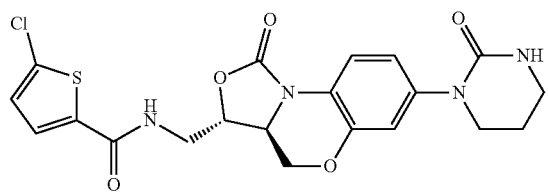 [SMILES: O=C(NC[C@@H]1OC(=O)N2c3ccc(N4CCCNC4=O)cc3OC[C@@H]12)c1ccc(Cl)s1]

The process for preparing compound 7 referred to embodiment 1, where the morpholin-3-one in step 2 was replaced with tetrahydropyrimidin-2(1H)-one. $^1$H NMR (400 MHz, DMSO-$d_6$) δ 9.00 (t, J=6.0 Hz, 1H), 7.69-7.75 (m, 2H), 7.20 (d, J=4.0 Hz, 1H), 6.85-6.95 (m, 2H), 6.55 (s, 1H), 4.47-4.62 (m, 2H), 3.94-4.10 (m, 2H), 3.71 (t, J=5.6 Hz, 2H), 3.56 (t, J=5.6 Hz, 2H), 3.20 (td, J=5.2, 2.0 Hz, 2H), 1.91 (t, J=6.0 Hz, 2H); LCMS (ESI) m/z: 463.0 (M+1).

Embodiment 4 The Process for Preparing Compound 8

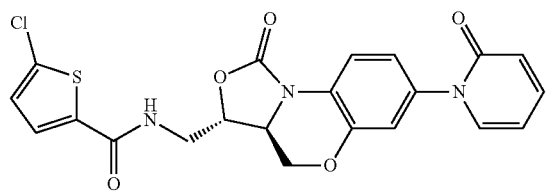 [SMILES: O=C(NC[C@@H]1OC(=O)N2c3ccc(-n4ccccc4=O)cc3OC[C@@H]12)c1ccc(Cl)s1]

The process for preparing compound 8 referred to the process in embodiment 1, where the morpholin-3-one in step 2 was replaced with pyridine-2(1H)-one. $^1$H NMR (400 MHz, DMSO-$d_6$) δ 9.01 (t, J=5.6 Hz, 1H), 7.95 (d, J=8.8 Hz, 1H), 7.72 (d, J=4.0 Hz, 1H), 7.59 (dd, J=6.8, 1.6 Hz, 1H), 7.49 (ddd, J=9.2, 6.8, 2.0 Hz, 1H), 7.21 (d, J=4.0 Hz, 1H), 7.06 (d, J=2.4 Hz, 1H), 7.01 (dd, J=8.8, 2.4 Hz, 1H), 6.45 (d, J=9.2 Hz, 1H), 6.29 (td, J=6.8, 1.2 Hz, 1H), 4.56-4.69 (m, 2H), 4.03-4.16 (m, 2H), 3.75 (t, J=5.6 Hz, 2H); LCMS (ESI) m/z: 458.1 (M+1).

Embodiment 5 The Process for Preparing Compound 30

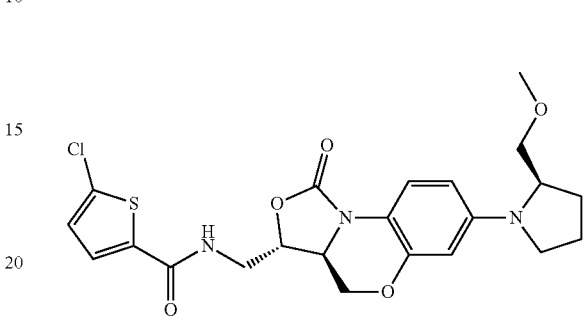

The process for preparing compound 30 referred to the process in embodiment 1, where the morpholine-3-one in step 2 was replaced with (R)-2-(methoxymethyl)pyrrolidine. $^1$H NMR (400 MHz, DMSO-$d_6$) δ 9.00 (t, J=5.4 Hz, 1H), 7.71 (d, J=4.0 Hz, 1H), 7.57 (d, J=9.2 Hz, 1H), 7.21 (d, J=4.0 Hz, 1H), 6.27 (dd, J=9.2, 2.8 Hz, 1H), 6.16 (d, J=2.8 Hz, 1H), 4.53-4.46 (m, 2H), 3.97-3.95 (m, 2H), 3.78-3.73 (m, 1H), 3.70 (t, J=5.6 Hz, 2H), 3.33-3.31 (m, 2H), 3.27 (s, 3H), 3.21-3.17 (m, 1H), 3.01-2.95 (m, 1H), 1.99-1.87 (m, 4H); LCMS (ESI) m/z: 478.1 (M+1).

Embodiment 6 The Process for Preparing Compound 34

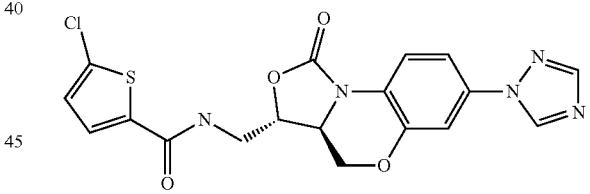

The process for preparing compound 34 referred to the process in embodiment 1, where the morpholine-3-one in step 2 was replaced with 1H-1,2,4-triazole. $^1$H NMR (400 MHz, DMSO-$d_6$) δ 9.27 (s, 1H), 9.05 (t, J=5.6 Hz, 1H), 8.22 (s, 1H), 8.02 (d, J=8.4 Hz, 1H), 7.75 (d, J=4.0 Hz, 3H), 7.52 (m, 2H), 7.22 (d, J=4.0 Hz, 1H), 4.64 (m, 2H), 4.14 (m, 2H), 3.75 (t, J=5.6 Hz, 2H); LCMS (ESI) ink: 432 (M+1).

In Vitro Activity Assay

The inhibitory ability of the compounds to be tested on Xa factor or other enzymes, such as thrombin or trypsin, in human or rats were determined by $IC_{50}$ values, wherein the $IC_{50}$ value was associated with the inhibition constant Ki. The purified enzyme was used in the chromogenic determination. The initial rate of hydrolysis of the chromogenic substrate was determined by the variation of absorbance at 405 nm in the linear part on time (usually 2 to 10 minutes after the addition of the substrate) at 37° C. by using FlexStation III (USA Molecular Instruments). By plotting a curve regarding the relative velocity of the hydrolysis (compared to the control group which was free of inhibition) on the logarithm of the concentration of the compounds and linear regression calculation, the concentration of the inhibitor leading to a 50% reduction of the rate of the hydrolysis of the substrate was determined. The enzyme inhibition constant (Ki) was calculated according to Cheng-Prusoff equation: $K_i = IC_{50}/(1+[S]/K_m)$, where [S] was the substrate concentration and Km was the meter-Mann's constant determined by the double reciprocal mapping method. The $IC_{50}$ values of the compounds were obtained by GraphPad Prism software. The curve is fitted by using the "shaped dose effect (variable slope)".

Human/Rat Coagulation Factor Xa Assay

The inhibitory activity on coagulation factor Xa activity in human or rats was measured by using Tris-HCl buffer (50 mM, pH 8.3, 150 mM NaCl). A buffer of 50 mL human coagulation factor Xa (Enzyme Research Laboratories, Inc; final concentration 8.36 nM) or a buffer of 50 µL rat coagulation factor Xa (Enzyme Research Laboratories, Inc; final concentration 57.5 nM) was added dropwise to the appropriate wells of the Greiner 384 microtiter plate to determine $IC_{50}$. The buffer containing 2 µL 2% (V/V) DMSO (control group which was free of inhibition) or various concentrations of the compounds to be tested were diluted in the buffer containing 2% (V/V) DMSO, and 48 µL buffer of the supporting base S-2222 (Chromogenix; chemical formula: Bz-Ile-Glu(γ-OR)-Gly-Arg-pNA.HCl R=H (50%), wherein R=CH$_3$ (50%)) was added, the final concentration was 0.172 mM. In this experiment, the compounds to be tested and the enzyme were incubated for 10 minutes, and then the substrate S-2222 was added to give a final volume of 100 µL to start the assay.

The compounds to be tested were regarded as being active when $K_i$<10 µM. The compounds whose $K_i$<1 µM were preferred in the present invention, more preferably $K_i$<0.1 µM, further more preferably $K_i$<0.01 µM, and further preferably $K_i$<0.001 µM. Determined by the above method, some compounds of the present invention were of $K_1$<0.1 µM, thus, the compounds of the present invention can be used as effective factor Xa inhibitors.

Human Thrombin Assay

The inhibitory activity on human thrombin was determined by using a buffer (10 mM HEPES buffer, pH 7.4, 2 mM CaCl$_2$). Appropriate wells in the Greiner 384 microtiter plate were used to determine $IC_{50}$. A buffer contained 50 µL human thrombin (Sigma; T8885), the final concentration of which was 0.05 NIH unit/mL. A buffer containing 2 µL 2% (V/V) DMSO (control group which was free of inhibition) or various concentration of the compound to be tested was diluted in the buffer containing 2% (V/V) DMSO. A buffer containing 48 µL substrate S-2238 (Chromogenix; Chemical formula: H-D-Phe-Pip-Arg-pNA.2HCl) was added, the final concentration was 30 µM. In this assay, the compound to be tested and the enzyme were pre-incubated for 10 minutes, the substrate was added to give a final volume of 100 µL to start the assay.

Human Trypsin Assay

The inhibitory activity on human trypsin was determined by using buffer (50 mM Tris, pH 8.2, and 20 mM CaCl$_2$). Appropriate wells in the Greiner 384 microtiter plate were used to determine $IC_{50}$. A buffer containing 50 µL human trypsin (Sigma; T6424), the final concentration was 0.39 BAEE unit/mL, a buffer containing 2 µL 2% (V/V) DMSO (control group which was free of inhibition) or various concentration of the compound to be tested was diluted in the buffer containing 2% (V/V) DMSO. A buffer containing substrate S-2222 (Chromogenix), the final concentration was 30 µM. In this assay, the compound to be tested and the enzyme were pre-incubated for 10 minutes and then 48 µL substrate was added to give a final volume of 100 µL to start the assay.

Prothrombin Assay

The activity of the compound to be tested against prothrombinase was determined by the production of thrombin. In summary, 12.5 µL human factor Xa was incubated in 10 mM HEPES buffer and pH 7.4, 2 mM CaCl$_2$, the final concentration was 0.5 nM, and 12.5 µL human blood platelets (1×10$^7$ mL$^{-1}$) was added at 37° C. After 10 mins, 25 µL prothrombin was added to initiate the reaction, the final concentration was 0.5 µM, a buffer containing 2 µL 2% (V/V) DMSO (control group which was free of inhibition) or various concentration of the compound was diluted in the buffer containing 2% (V/V) DMSO. After 20 minutes, 48 µL substrate S-2238 (Chromogenix) was added until the final concentration was 50 µM to determine thrombin activity.

TABLE 1

The results of the compound of the present invention screened in vitro

| Compound | hfXa $K_i$ (nM) | rfXa $K_i$ (nM) | Thrombin $K_i$ (nM) | Trypsin $K_i$ (nM) | Prothrombin $K_i$ (nM) |
|---|---|---|---|---|---|
| 1 | 1.01 | 2.87 | >1000 | >20000 | 0.47 |
| 2 | 1.93 | 4.45 | >1000 | >20000 | 4.22 |
| 7 | 4.135 | 16.49 | >1000 | >20000 | 4.41 |
| 8 | 1.92 | 3.17 | >1000 | >20000 | 0.9 |
| 30 | 9.71 | 21.47 | >1000 | >20000 | 16.17 |
| 34 | 105.94 | / | / | / | / |

Conclusion: the compounds of the present invention showed a potent anticoagulant activity due to the specific inhibitory activity on coagulation factor Xa thereof.

What is claimed is:

1. A process for preparing the compound having a structure of formula (II), which comprises the following step,

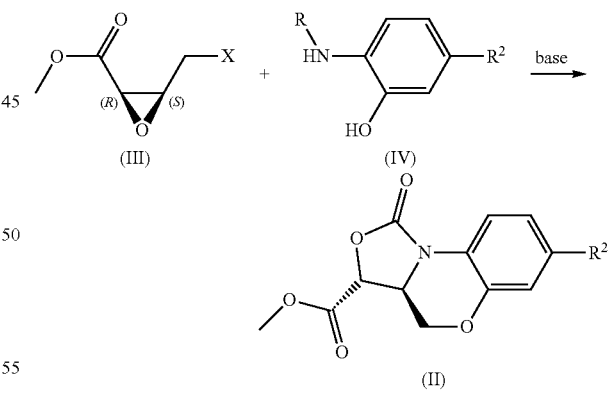

wherein,

R is an amino-protecting group, or selected from an alkoxycarbonyl, or Cbz, Boc, Fmoc, Alloc, Teco, methoxycarbonyl or ethoxycarbonyl;

X is F, Cl, Br or I;

R$^2$ is selected from optionally substituted 5- or 6-membered cyclic amino or heterocyclic amino, "hetero" represents O, N, C(=O) or C(=O)NH, the substituent is independently selected from a C$_{1-4}$ alkyl or a heteroalkyl, or, $R^2$ is selected from

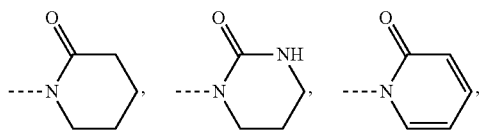

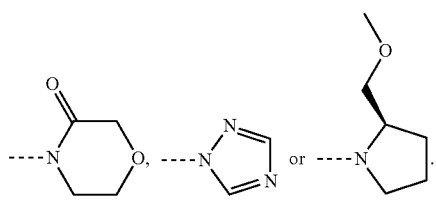

2. The process of claim 1, wherein the base is selected from an alkali metal base, an alkaline earth metal base or an organometallic base.

3. The process of claim 1, wherein a molar ratio of the compound (IV) to the base is 1:1 to 5, or 1:2 to 3;
   a molar ratio of the compound (III) to the compound (IV) is 1:1 to 2;
   temperature of the reaction is −10 to 50° C., or 0 to 30° C., and/or,
   the reaction time is 5 to 200 hours, or 10 to 100 hours, or 16 to 48 hours.

4. The process of claim 1, wherein the reaction is carried out in a solvent, the solvent is selected from an amide solvent, an ether solvent or any mixture thereof;
   or, an amount of the solvent is 10 to 50 times the weight of the compound (IV), or 15 to 20 times.

5. A process for preparing the compound having a structure of formula (I), which comprises the following step:

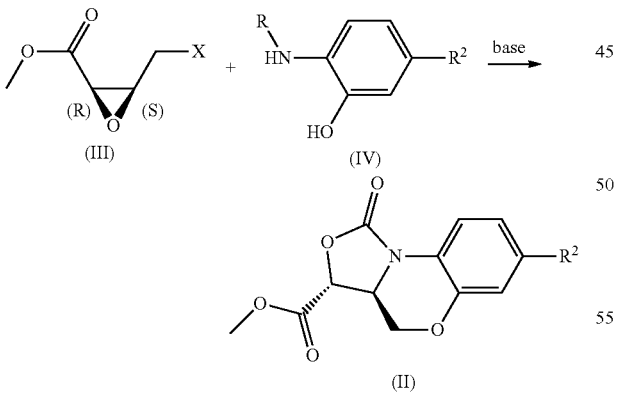

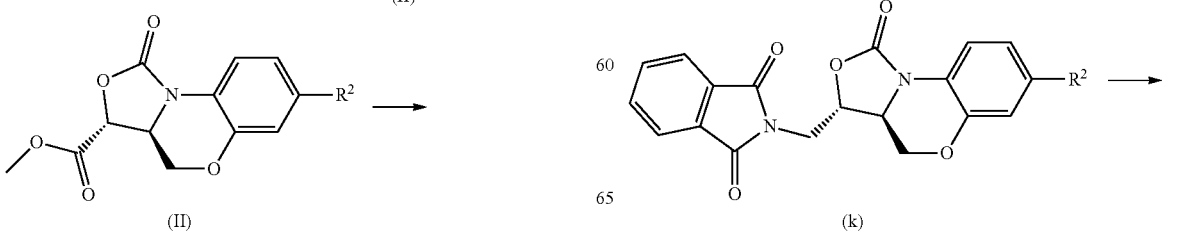

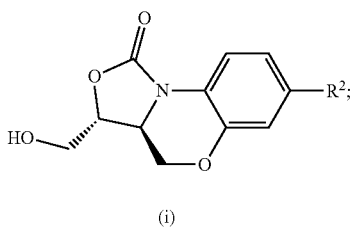

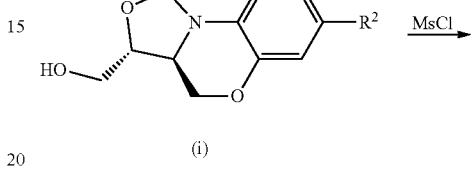

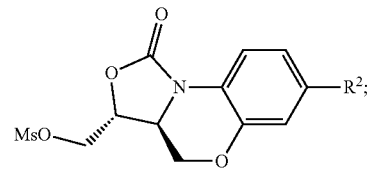

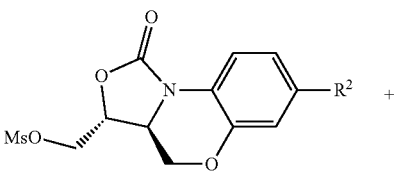

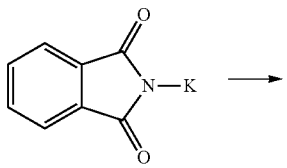

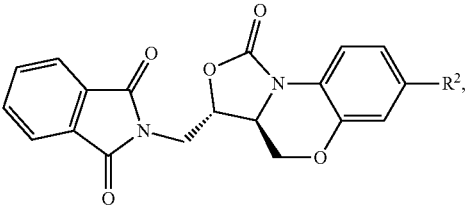

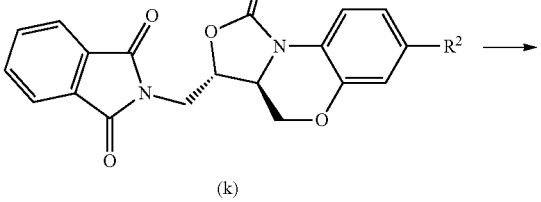

-continued

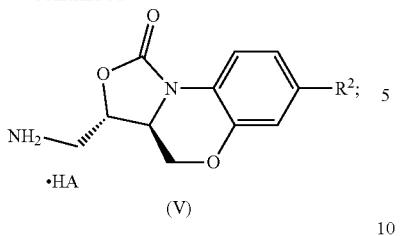

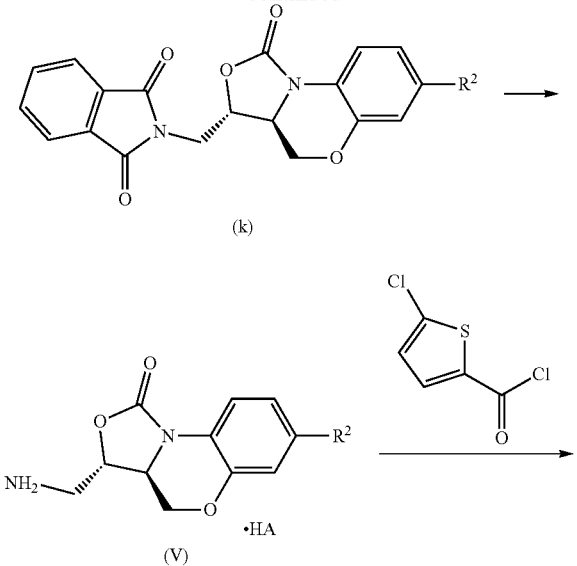

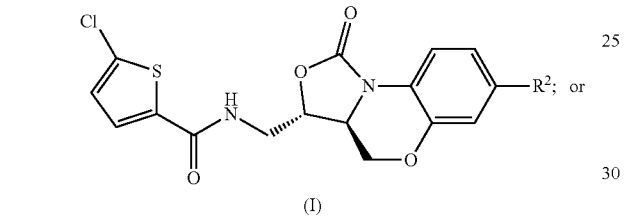

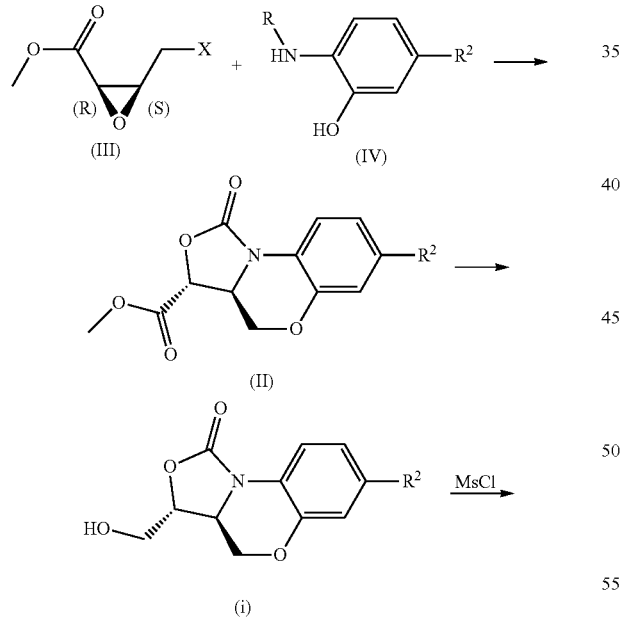

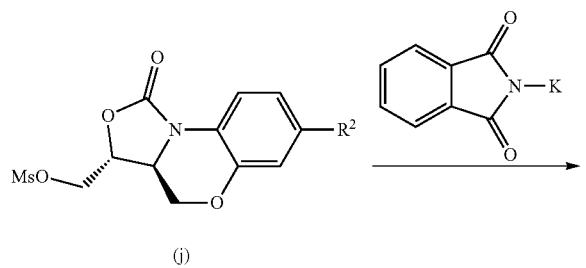

wherein HA is selected from an organic acid or an inorganic acid, or HA is selected from hydrochloric acid, sulfuric acid, oxalic acid, citric acid, maleic acid or fumaric acid.

6. A compound having the structure of formula (II) or (V),

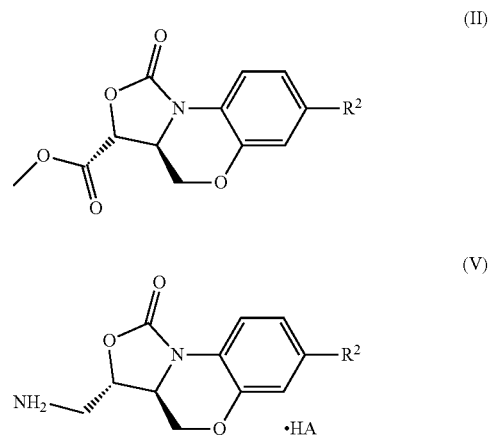

wherein,

R² is selected from optionally substituted 5- or 6-membered cyclic amino or heterocyclic amino, "hetero" represents O, N, C(=O) or C(=O)NH, the substituent is independently selected from a $C_{1-4}$ alkyl or a heteroalkyl;

or, R² is selected from

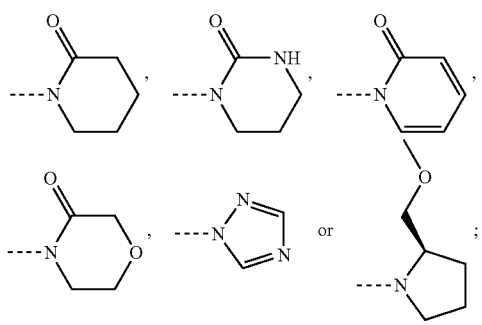

HA is selected from an organic acid or an inorganic acid; or HA is selected from hydrochloric acid, sulfuric acid, oxalic acid, citric acid, maleic acid or fumaric acid.

7. The process of claim 2, wherein the base is selected from an alkali metal base, an alkaline earth metal base or an organometallic base, the alkali metal base is selected from lithium hydroxide, sodium hydroxide, potassium hydroxide, cesium hydroxide, sodium carbonate, potassium carbonate, cesium carbonate, sodium bicarbonate and/or potassium bicarbonate;

or, the alkaline earth metal base is selected from sodium hydride, potassium hydride and/or calcium hydride;

or, the organometallic base is selected from sodium methoxide, lithium tert-butoxide, sodium tert-butoxide, potassium tert-butoxide, sodium ethoxide and/or aluminum isopropoxide.

8. The process of claim 1, wherein the reaction is carried out in a solvent, the solvent is selected from an amide solvent, an ether solvent or any mixture thereof; the amide solvent is selected from DMF or DMAC, or, the ether solvent is selected from tetrahydrofuran, methyl tetrahydrofuran, dioxane or methyl t-butyl ether.

* * * * *